US011242408B2

(12) United States Patent
Ceylan et al.

(10) Patent No.: US 11,242,408 B2
(45) Date of Patent: Feb. 8, 2022

(54) MONOCLONAL ANTIBODY SPECIFIC FOR GAMMA-GLUTAMYL-L-EPSILON-LYSINE FOR THE MONITORING OF APOPTOSIS

(71) Applicants: ADVANCED BIODESIGN, Saint-Priest (FR); Jean-Yves Quash, Gometz la Ville (FR)

(72) Inventors: Ismail Ceylan, Saint-Priest (FR); Gerry Quash, Saint-Priest (FR); Mileidys Perez-Alea, Saint-Priest (FR); Guillaume Martin, Saint-Priest (FR)

(73) Assignee: ADVANCED BIODESIGN, Saint-Priest (FR)

( * ) Notice: Subject to any disclaimer, the term of this patent is extended or adjusted under 35 U.S.C. 154(b) by 649 days.

(21) Appl. No.: 16/309,860

(22) PCT Filed: Jun. 14, 2017

(86) PCT No.: PCT/EP2017/064553
§ 371 (c)(1),
(2) Date: Dec. 13, 2018

(87) PCT Pub. No.: WO2017/216227
PCT Pub. Date: Dec. 21, 2017

(65) Prior Publication Data
US 2019/0169313 A1 Jun. 6, 2019

(30) Foreign Application Priority Data

Jun. 14, 2016 (EP) ..................................... 16305724

(51) Int. Cl.
*A61K 39/395* (2006.01)
*C07K 16/00* (2006.01)
*C07K 16/44* (2006.01)
*G01N 33/53* (2006.01)
*G01N 33/68* (2006.01)
*G01N 33/558* (2006.01)

(52) U.S. Cl.
CPC ......... *C07K 16/44* (2013.01); *G01N 33/5308* (2013.01); *G01N 33/558* (2013.01); *G01N 33/6893* (2013.01); *C07K 2317/34* (2013.01); *G01N 2410/00* (2013.01); *G01N 2800/26* (2013.01)

(58) Field of Classification Search
None
See application file for complete search history.

(56) References Cited

FOREIGN PATENT DOCUMENTS

WO          96/40985 A1     12/1996

OTHER PUBLICATIONS

Thomas et al. (J. of Immunological Methods 292, 2004, pp. 83-95) (Year: 2004).*
Kunik, V., et al. "Structural Consensus among Antibodies Defines the Antigen Binding Site" PLOS Computational Biology 8(2):1-12 (Feb. 2012).
Torres, M., et al. "The immunoglobulin constant region contributes to affinity and specificity" Trends In Immunology 29(2):91-97 (Jan. 10, 2008).
Communication (International Search Report and Written Opinion) issued by the International Searching Authority in International Patent Application No. PCT/EP2017/064553, dated Jul. 20, 2017, 10 pages total.
Communication (Extended European Search Report) issued by the European Patent Office in European Application No. 16305724.3, dated Jan. 16, 2017, 5 pages total.
Chan, T. et al., "Early Diagnosis of Sepsis Using Serum Biomarkers" Expert Reviews Molecular Diagnostics (2011) vol. 11, No. 5, pp. 487-496, 18 pages total.
Johnson, G.V.W. et al., "Immunoblot Analysis Reveals that Isopeptide Antibodies Do Not Specifically Recognize the ϵ-(γ-glutamyl)lysine Bonds Formed by Transglutaminase Activity" Journal of Neuroscience Methods (2004) vol. 134, pp. 151-158.
Griffin, M. et al., "Detection of ϵ-(γ-glutamyl)lysine" Molecular and Cellular Biochemistry (1984) vol. 58, pp. 37-49.
Sárvári, M. et al., "Competitive Enzyme-Linked Immonosorbent Assay for Nϵ-(γ-glutamyl)lysine" Analytical Biochemistry (2002) vol. 311, pp. 187-190.
Schwameis, M. et al., "D-Dimer and Histamine in Early Stage Bacteremia: A Prospective Controlled Cohort Study" European Journal of Internal Medicine (2015) vol. 26, pp. 782-786.
Thomas, V. et al., "Definition of the Fine Specificity of the Monoclonal Antibody 81D4: Its Reactivity with Lysine and Polyamine Isopeptide Cross-Links" Journal of Immunological Methods (2004) vol. 292, No. 1-2, pp. 83-95.
Vincent, J-L. et al., "Diagnostic and Prognostic Markers in Sepsis" Expert Reviews Anti-Infective Therapy (2013) vol. 11, No. 3, pp. 265-275.

* cited by examiner

*Primary Examiner* — Meera Natarajan
(74) *Attorney, Agent, or Firm* — Troutman Pepper Hamilton Sanders LLP

(57) ABSTRACT

The present invention concerns an ex vivo method for the monitoring of apoptosis which is based on the detection of free gamma-glutamyl-L-epsilon-Lysine (GGEL) in a biological sample of a subject with a monoclonal antibody specific to GGEL. The invention also relates to the monoclonal antibody specific to GGEL, as well as to diagnostic kits containing such a ligand.

15 Claims, 8 Drawing Sheets

Figure 1:
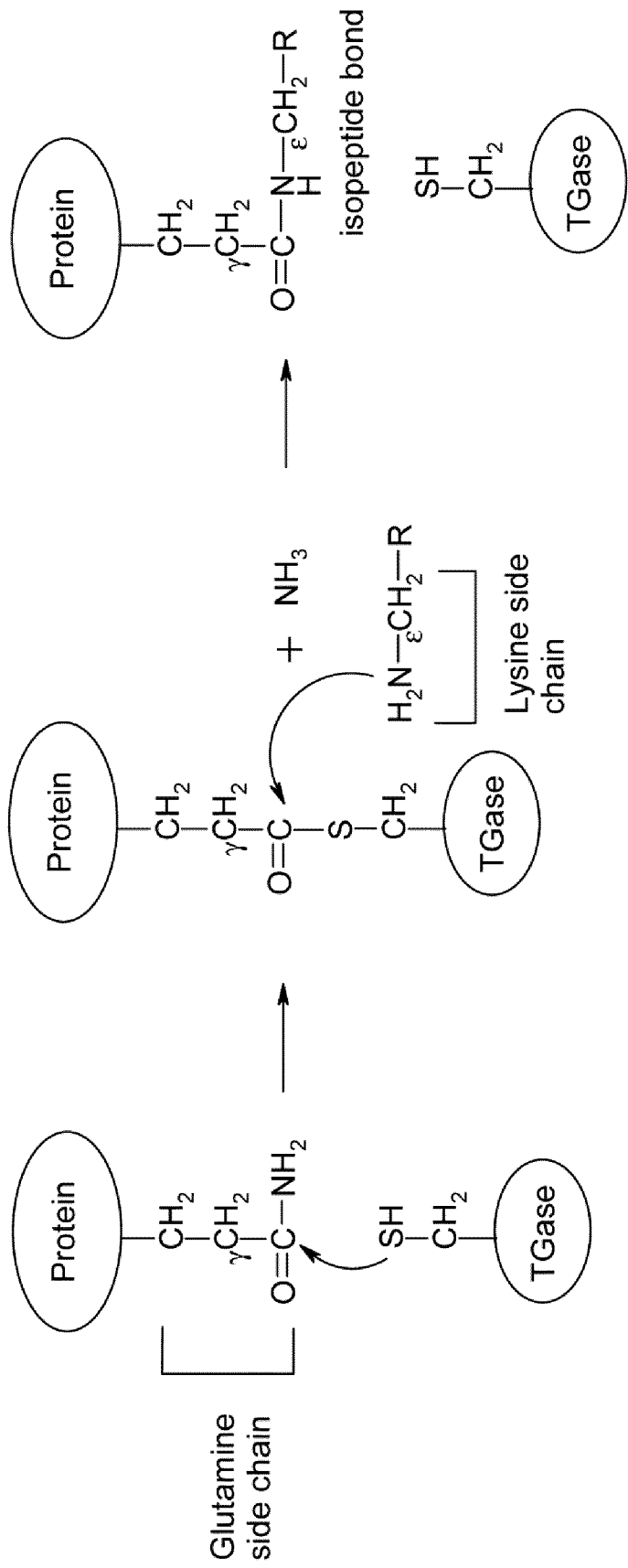

Specification includes a Sequence Listing.

MONOCLONAL ANTIBODY SPECIFIC FOR GAMMA-GLUTAMYL-L-EPSILON-LYSINE FOR THE MONITORING OF APOPTOSIS

CROSS-REFERENCE TO RELATED APPLICATIONS

This application is a National Stage of International Application No. PCT/EP2017/064553, filed Jun. 14, 2017, this application, in turn, claims priority to European Patent Application No. 16305724.3, filed Jun. 14, 2016, all of which applications are incorporated herein by reference.

The present invention concerns an ex vivo method for the monitoring of apoptosis which is based on the detection of free gamma-glutamyl-L-epsilon-Lysine (GGEL) in a biological sample of a subject with a monoclonal antibody specific to GGEL. The invention also relates to the monoclonal antibody specific to GGEL, as well as to diagnostic kits containing such a ligand.

BACKGROUND

Apoptosis is a tightly regulated process of programmed cell death that occurs in multicellular organisms. Apoptosis is a fundamental mechanism inherent in cells for the elimination of senescent and damaged cells as well as for the proper functioning of the immune system. Contrary to necrosis in which cell swelling takes place, apoptosis is characterised by cell shrinkage, condensation of chromatin, fragmentation of DNA into multiples of 120 base pairs and cross-linking of cytoplasmic constituents into apoptotic bodies that are detergent insoluble.

Malfunction of the death machinery intrinsic to every cell may play a primary or secondary role in various diseases, with essentially too little or too much apoptosis (or apoptosis occurring in the wrong place and/or at the wrong time) leading to proliferative or degenerative diseases, respectively. The dysregulation of apoptosis can indeed lead to the destruction of normal tissues in a variety of disorders, including autoimmune and neurodegenerative diseases (too much apoptosis) or the growth of tumors (too little apoptosis). In addition, effective therapy of tumors requires the iatrogenic induction of programmed cell death by radiation, chemotherapy, or both (Blankenberg F, G., J Nucl Med June 2008 vol. 49 no. Suppl 2 81 S-95S).

Non-invasive imaging methods have been developed to monitor in vivo apoptosis, using tracers that bind to the plasma membrane of cells during apoptosis (Blankenberg F, G., J Nucl Med June 2008 vol. 49 no. Suppl 2 81S-95S; Brauer M., Progress in Neuro-pyschopharmacology & Biological Psychiatry 2003 April; 27(2):323-31). However these methods notably rely on magnetic resonance imaging (MRI), positron emission tomography (PET) or single-photon emission computed tomography (SPECT), and, as a consequence, are not readily available.

"N-ε-(γ-glutamyl)-L-lysine", also referred to as "gamma-glutamyl-L-epsilon-Lysine", "Nε-(γ-glutamyl)-lysine" or "GGEL", is an isopeptide produced by transglutaminase reaction.

Tissue transglutaminase is a $Ca^{2+}$ dependent cytoplasmic enzyme normally present in many cells. However, the enzyme is not activated by normal $Ca^{2+}$ levels found in cells. Activation of the enzyme in vivo does not occur until the intracellular free $Ca^{2+}$ concentration increases which typically occurs, for example, when lymphocytes undergo activation-induced apoptosis. Tissue transglutaminase is activated in cells undergoing apoptosis to form N-ε-(γ-glutamyl)-lysine isopeptide bonds between proteins. Apoptotic bodies formed during the end stage of apoptosis possess a surface marker, phosphatidyl serine (PS), which represents a recognition marker for elimination by macrophages. But this elimination takes place very rapidly hence, lymphocyte apoptosis is under estimated (Mc Carthy et al., 1998 Curr. Top. Dev. Biol. Vol 36 p 259-278). On the contrary the peptide bonds of proteins in apoptotic bodies can be cleaved, whereas their N-ε-(γ-glutamyl)-lysine isopeptide bonds are resistant to proteolysis and are released in the form of free N-ε-(γ-glutamyl)-lysine isopeptides into the blood stream.

Accordingly GGEL ("released GGEL" or "free GGEL") results from the phagocytosis of cells induced into apoptosis and is the final product of degradation of cross-linked cellular proteins by cellular proteases.

A method for quantitatively measuring apoptosis has been described in international patent application WO 96/40985. The method applies coupled enzyme reactions to release lysine and convert lysine to saccharopine in a process in which NADH is consumed, and NADH consumption is then quantitated.

However, there is still a need for a rapid, reproducible, quantitative method to detect in vivo levels of apoptosis, in a clinical setting, such as an immunoassay based method.

A mouse monoclonal antibody AB424 directed to GGEL is available from Abcam (Cambridge, UK; catalog number AB424). The AB424 was isolated as described in Thomas et al. 2004, J. Immunol. Methods 292, 83-95. However, AB424 cross-reacts with isopeptide $N^1,N^8$bis(gamma-glutamyl) spermidine. Polyamine crosslinks are thus likely to interfere with detection of GGEL in an immunoassay using antibody.

Development of an immunoassay based method for monitoring in vivo apoptosis has thus been hampered by the lack of anti-GGEL specific monoclonal antibody.

SUMMARY OF THE INVENTION

The invention relates to an isolated monoclonal antibody specific for gamma-glutamyl-L-epsilon-Lysine (GGEL) which comprises CDR-H1 of sequence SEQ ID NO:3, CDR-H2 of sequence SEQ ID NO:4, CDR-H3 of sequence SEQ ID NO:5, CDR-L1 of sequence SEQ ID NO:6, CDR-L2 of sequence SEQ ID NO:7, and CDR-L3 of sequence SEQ ID NO:8.

The invention also relates to a method for measuring the level of gamma-glutamyl-L-epsilon-Lysine (GGEL) in a sample, which comprises:
  a) contacting a sample with the monoclonal antibody specific for GGEL according to the invention; and
  b) measuring the level of complexes formed with the monoclonal antibody specific for GGEL according to the invention;

wherein the level of GGEL in the sample is deduced from the level of complexes formed with the monoclonal antibody specific for GGEL.

The invention further relates to an ex vivo method for monitoring apoptosis in a subject, which comprises:
  a) measuring the level of free gamma-glutamyl-L-epsilon-Lysine (GGEL) isopeptide in a plasma sample of the subject with an immunoassay using the monoclonal antibody specific for GGEL according to the invention;
  b) comparing said measured level of free GGEL with a control; and
  c) monitoring apoptosis in said subject based on the comparison with the control.

The invention also relates to the use of a monoclonal antibody specific for gamma-glutamyl-L-epsilon-Lysine (GGEL) according to the invention for the monitoring of apoptosis. The invention further relates to a method for monitoring effectiveness of an apoptosis inducing treatment in a subject, which comprises:
  a) measuring the level of free gamma-glutamyl-L-epsilon-Lysine (GGEL) isopeptide in a plasma sample of a subject undergoing an apoptosis inducing treatment, with a method according to claim 4;
  b) repeating the measurement of step a) in time; and
  c) deducing that the apoptosis inducing treatment is effective if the level of free GGEL increases over time, or that the apoptosis inducing treatment is ineffective if the level of free GGEL is unchanged or decreases over time.

The invention further provides for a method for monitoring effectiveness of an apoptosis inhibiting treatment in a subject is provided, which comprises:
  a) measuring the level of free gamma-glutamyl-L-epsilon-Lysine (GGEL) isopeptide in a plasma sample of a subject undergoing an apoptosis inhibiting treatment, with a method according to claim 4;
  b) repeating the measurement of step a) in time; and
  c) deducing that the apoptosis inhibiting treatment is effective if the level of free GGEL decreases over time, or that the apoptosis inhibiting treatment is ineffective if the level of free GGEL is unchanged or increases over time.

The invention is also drawn to a method of treating a disease associated with dysregulated apoptosis in a subject in need thereof, which comprises:
  a) administering an apoptosis modulating treatment to a subject treating suffering from a disease associated with dysregulated apoptosis
  b) monitoring if said treatment modulates apoptosis in the subject by implementing the method of monitoring of apoptosis according to claim 5 or 9; and
  c) continuing or modifying the apoptosis modulating treatment based on the result of monitoring of step b).

Also provided is a kit for the monitoring of apoptosis which comprises:
  a) the monoclonal antibody directed to gamma-glutamyl-L-epsilon-Lysine (GGEL) according to the invention; and
  b) a control.

In another aspect, the invention relates to a method of treating sepsis in a subject in need thereof, which comprises:
  a) diagnosing sepsis in a subject by an ex vivo method of diagnostic of sepsis according to the invention; and
  b) administering a therapeutic treatment against sepsis to the subject diagnosed as suffering from sepsis.

The invention is also drawn to a lateral flow immunoassay device which comprises a monoclonal antibody directed to gamma-glutamyl-L-epsilon-Lysine (GGEL) according to the invention.

DESCRIPTION OF THE INVENTION

"N-ε-(γ-glutamyl)-L-lysine", also referred to as "gamma-glutamyl-L-epsilon-Lysine", "Nε-(γ-glutamyl)-lysine" or "GGEL", denotes an isopeptide produced by transglutaminase reaction and which is released as a result of the phagocytosis of cells induced into apoptosis. GGEL (or free GGEL) is the final product of degradation of cross-linked cellular proteins by cellular proteases.

As used herein "subject" denotes a mammal, such as a feline, a canine, a rodent, or a primate. Preferably a subject is intended for a human, in particular a child, a woman, or a man.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of"). Furthermore the indefinite article "a" or "an" does not exclude a plurality. The mere fact that certain features are recited in different embodiments does not indicate that a combination of these features cannot be used.

Detection of Gamma-Glutamyl-L-Epsilon-Lysine (GGEL)

GGEL is detected or the level of GGEL is measured using a monoclonal antibody specific to GGEL.

An "antibody" may be a natural or conventional antibody in which disulfide bonds link two heavy chains to each other and each heavy chain is linked to a light chain by a disulfide bond. The light chain includes two domains or regions, a variable domain (VL) and a constant domain (CL). The heavy chain includes four domains, a variable domain (VH) and three constant domains (CH1, CH2 and CH3, collectively referred to as CH). The specificity of the antibody resides in the structural complementarity between the antibody combining site and the antigenic determinant. Antibody combining sites are made up of residues that are primarily from the hypervariable or "complementarity determining regions" (CDRs). The light and heavy chains of an immunoglobulin each have three CDRs, designated CDR-L1, CDR-L2, CDR-L3 and CDR-H1, CDR-H2, CDR-H3, respectively. A conventional antibody antigen-binding site, therefore, includes six CDRs, comprising the CDR set from each of a heavy and a light chain V region.

"Framework Regions" (FRs) refer to amino acid sequences interposed between CDRs, i.e. to those portions of immunoglobulin light and heavy chain variable regions that are relatively conserved among different immunoglobulins in a single species. The light and heavy chains of an immunoglobulin each have four FRs, designated FR-L1, FR-L2, FR-L3, FR-L4, and FR-H1, FR-H2, FR-H3, FR-H4, respectively.

In the context of the invention, CDR/FR definition in an immunoglobulin light or heavy chain is to be determined based on IMGT definition (Lefranc et al. Dev. Comp. Immunol., 2003, 27(1):55-77; www.imgt.org).

As used herein, the term "antibody" denotes conventional antibodies and antigen binding fragments thereof, as well as chimeric, humanised, bispecific or multispecific antibodies.

The term "monoclonal antibody" or "mAb" as used herein refers to an antibody molecule of a single primary structure that is directed against a specific antigen, and is not to be construed as requiring production of the antibody by any particular method. A monoclonal antibody may be produced by a single clone of B cells or hybridoma, but may also be recombinant, i.e. produced by protein engineering.

"Fragments" of (conventional) antibodies comprise a portion of an intact antibody, in particular the antigen binding region or variable region of the intact antibody. Examples of antibody fragments include Fv, Fab, F(ab')2, Fab', dsFv, (dsFv)2, scFv, sc(Fv)2, diabodies, bispecific and multispecific antibodies formed from antibody fragments.

The invention provides an isolated monoclonal antibody specific to GGEL which comprises CDR-H1 of sequence GYTFTSY (SEQ ID NO:3), CDR-H2 of sequence NPSNGG (SEQ ID NO:4), CDR-H3 of sequence SGLLLWSPWFAY (SEQ ID NO:5), CDR-L1 of sequence RASENIYSYLA (SEQ ID NO:6), CDR-L2 of sequence NAKTLAE (SEQ ID NO:7), and CDR-L3 of sequence QHHYGTPFT (SEQ ID NO:8).

In an embodiment, said isolated antibody comprises a variable domain of heavy chain ($V_H$) consisting of sequence QVQLQQPGTELVKPGASVKLSCKASGYTFTSYWMHWVKQRPGQGLEWIGNINPSNGGTNYNEKFKSKATLTVDKSSSTAYMQLSSLTSEDSAVYYCARSGLLLWSPWFAYWGQGT LVTVS (SEQ ID NO:1), or a sequence at least 85% identical to SEQ ID NO:1.

In another embodiment, said isolated antibody comprises a variable domain of light chain ($V_L$) consisting of sequence DIQMTQSPASLSASVGETVTITCRASENIYSYLAWYQQKQGKSPQLLVYNAKTLAEGVPSRFSGSGSGTQFSLKINSLQPEDFGSYYCQHHYGTPFTFGSGTKLEIKR (SEQ ID NO:2), or a sequence at least 85% identical to SEQ ID NO:2.

In still another embodiment, said isolated antibody comprises a $V_H$ consisting of sequence SEQ ID NO:1 or a sequence at least 85% identical thereto, and a $V_L$ consisting of sequence SEQ ID NO:2 or a sequence at least 85% identical thereto.

The isolated antibody specific to GGEL is in particular the so-called 1G1h1 antibody which comprises a $V_H$ consisting of sequence SEQ ID NO:1, and a $V_L$ consisting of sequence SEQ ID NO:2.

A sequence "at least 85% identical" to a reference sequence is a sequence having, on its entire length, 85%, or more, in particular 90%, 91%, 92%, 93%, 94%, 95%, 96%, 97%, 98% or 99% sequence identity with the entire length of the reference sequence.

A percentage of "sequence identity" may be determined by comparing the two sequences, optimally aligned over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison is conducted by global pairwise alignment, e.g. using the algorithm of Needleman and Wunsch J. Mol. Biol. 48:443 (1970). The percentage of sequence identity can be readily determined for instance using the program Needle, with the BLOSUM62 matrix, and the following parameters gap-open=10, gap-extend=0.5.

The isolated antibody according to the invention binds to ε-(γ-glutamyl)-lysine in the form of free N-ε-(γ-glutamyl)-lysine isopeptide. In particular, the antibody binds to one or more, preferably all of the GGEL-like proteins as disclosed in Table 2.

Preferably the antibody is specific to GGEL, i.e. it is not significantly cross-reactive with one or more, preferably all of (i) acetylated lysine (such as present in acetylated bovine serum albumin (BSA), (ii) polyamine crosslink (such as present in spermidine (Spd) coupled to polyGlutamic acid), or (iii) Ubiquitinylation/Sumolytation crosslink (such as present in Boc-Gly-BSA) (see Table 3).

A monoclonal antibody binding to antigen 1 (Ag1) is "cross-reactive" to antigen 2 (Ag2) when the $IC_{50}$s are in a similar range for both antigens. In the present application, a monoclonal antibody binding to Ag1 is cross-reactive to Ag2 when the ratio of affinity of Ag2 to affinity of Ag1 is equal or less than 10, affinities being measured with the same method for both antigens.

A monoclonal antibody binding to Ag1 is "not significantly cross-reactive" to Ag2 when the affinities are very different for the two antigens. Affinity for Ag2 may not be measurable if the binding response is too low. In the present application, a monoclonal antibody binding to Ag1 is not significantly cross-reactive to Ag2, when the ratio of affinity of Ag2 to affinity of Ag1 is equal or more than 10.

"Affinity" is defined, in theory, by the equilibrium association between the antibody and the antigen. It can be experimentally assessed by a variety of known methods, such as measuring association and dissociation rates with surface plasmon resonance or measuring the $EC_{50}/IC_{50}$ in an immunochemical assay (ELISA, FACS). In these assays, the $EC_{50}/IC_{50}$ is the concentration of the antibody which induces a response halfway between the baseline and maximum after some specified exposure time on a defined concentration of antigen by ELISA (enzyme-linked immuno-sorbent assay) or cell expressing the antigen by FACS (Fluorescence Activated Cell Sorting).

A mouse monoclonal antibody AB424 directed to GGEL is available from Abcam (Cambridge, UK; catalog number AB424) significantly cross-react with isopeptide $N^1,N^8$bis (gamma-glutamyl) spermidine, contrary to AB424. The AB424 was isolated as described in Thomas et al. 2004, J. Immunol. Methods 292, 83-95.

In an embodiment, the level of GGEL is measured by immunoassay, binding assay, or chromatography.

An immunoassay for GGEL measurement typically measures concentration of GGEL through the use of an antibody. The antibody may be immobilized on a solid support. Antibodies specific to GGEL may be used in a range of immunological assays including competitive and non-competitive assay systems using techniques such as Western blotting, radioimmunoassay such as RIA (radio-linked immunoassay), ELISA (enzyme linked immunosorbent assay), "sandwich" immunoassays, "indirect" immunoassays, "competitive" immunoassays, immunoprecipitation assays, immunodiffusion assays, agglutination assays, complement-fixation assays, immunoradiometric assays, fluorescent immunoassays, e.g. FIA (fluorescence-linked immunoassay), chemiluminescence immunoassays, chromatographic immunoassays, electrochemiluminescence immunoassay (ECLIA) and protein A immunoassays.

In an embodiment, the level of GGEL is measured by an ELISA, in indirect, competitive or sandwich format.

For instance, a competitive ELISA can be implemented by absorbing the anti-GGEL antibody on microtiter plate (e.g. in a 50 mM bicarbonate solution pH 9.50), incubating the plates (e.g. overnight at laboratory temperature), followed by saturation of the solid support (e.g. using a phosphate buffer 0.1 M supplemented of BSA 0.5% and sucrose 5%). Samples to be analysed, optionally diluted, are added in presence of labelled GGEL, for instance with a GGEL-HRP solution for 1 hour at 37° C. For use as a standard, BZGO (N-alpha-Carbobenzyloxy-Glutamic acid Methyl Ester (Z-GluOme) coupled to BSA) with a precise number of GGEL "coated" can be diluted two by two. After washes (e.g. three washes with PBST), revelation is performed (e.g. using TMB for 5 minutes and reaction is stopped using H2SO4, 2N). Absorbance values are determined at 450 nm with e.g. Spectramax i3® automated microplate reader (Molecular Devices, Sunnydale, USA). GGEL quantification can be performed using standard plotted on a 4 parameters line using GrapPad Prism version 5.0 (GraphPad software, San Diego, USA). The threshold for positivity of results is determined considering the mean of the blank added to 3.33 standard deviation.

Alternatively, a competitive ELISA can be implemented by absorbing BSA-GGEL on microtiter plate, e.g. at a concentration of 10 µg/mL in a 50 mM bicarbonate solution pH 9.50. Plates are incubated, e.g. overnight at laboratory temperature, followed by saturation, e.g. with a phosphate buffer 0.1 M supplemented of BSA 0.5% and sucrose 5%. Samples to be analysed, optionally diluted, are added in presence of anti-GGEL antibody solution, e.g. for 1 hour at 37° C. For use as a standard, BZGO with a precise number of GGEL "coated" can be diluted two by two. After washes, e.g. three washes with PBST, secondary antibody (e.g. diluted 1 in 2000 PBST) is incubated for e.g. 30 minutes at 37° C. Revelation is performed (e.g. using TMB for 5 minutes and reaction is stopped using $H_2SO_4$, 2N). Absorbance values are determined at 450 nm with e.g. Spectramax i3® automated microplate reader (Molecular Devices, Sunnydale, USA). GGEL quantification can be performed using standard plotted on a 4 parameters line using GrapPad Prism version 5.0 (GraphPad software, San Diego, USA). The threshold for positivity of results was determined considering the mean of the blank added to 3.33 standard deviation.

In another embodiment, the level of GGEL is measured by a Lateral Flow ImmunoAssay (LFIA). LFIA is a chromatographic immunoassay.

In another embodiment, the level of GGEL is measured by Particles Gel ImmunoAssay (PaGIA) or Coomb's assay. In these assays, the separation between bound and unbound anti-GGEL ligand is obtained by centrifugation through a size exclusion gel column.

In indirect competitive Coomb's assay, the sample (serum) is pre-incubated with anti-GGEL antibody, during a few minutes, and then red blood cells (RBC) sensitized with GGEL (e.g. BSA-GGEL) are added. After a second incubation, a centrifugation through a size exclusion gel column, generally in a microtube, is performed to discriminate between bound and unbound antibody. In absence of GGEL in the sample, antibodies bind to sensitized RBC and form a high-molecular complex. After the centrifugation, this complex will remain on the top of the column. When GGEL is present in the sample above the lower detectable concentration level, antibody will bind to the GGEL present in the sample instead of binding RBC sensitized with GGEL. After centrifugation, no agglutination is observed. Interpretation of assay results depends on the presence or not of the high molecular complex formed by the interaction between anti-GGEL antibodies and RBC sensitized with GGEL. Strong negative reaction (−) corresponds to a complete agglutination, seen as a red line on top of the gel or just below the surface of the gel, or by agglutinates distributed only within the upper part of the gel. Weak positive reaction (+) can be distinguished when some RBC reach the bottom of the microtube with agglutinates still visible in the upper part of the gel, or throughout the gel. A positive reaction (+) corresponds to a complete sedimentation of the erythrocytes as a pellet at the bottom of the microtube, and no agglutinated particles visible within the gel.

Monitoring of Apoptosis

An ex vivo method for monitoring apoptosis in a subject is provided which comprises:

a) measuring the level of free gamma-glutamyl-L-epsilon-Lysine (GGEL) isopeptide in a plasma sample of the subject with the monoclonal antibody directed GGEL according to the invention;

b) comparing said measured level of free GGEL with a control; and c) monitoring apoptosis in said subject based on the comparison with the control.

The control may be a single value or a range of values, which is determined, based on the level of free GGEL in plasma samples from a subject or population of healthy subjects, or from a subject or population of subjects suffering from a disease associated with dysregulated apoptosis. Typically, the analysed population can be divided into quantiles based on the measured level of free GGEL. The control can be defined as the median, or the second tertile, or the second or third quartile, or the third or fourth quintile etc. . . . . . The control can also be defined as the mean free GGEL level in plasma samples from a subject or population of healthy subjects, or from a subject or population of subjects suffering from a disease associated with dysregulated apoptosis.

The control can also be determined by analysing a plasma sample from the same subject at an earlier time point, for instance prior to onset of the disease associated with dysregulated apoptosis.

Comparison with a control may also be performed by comparing the measured level of free GGEL with the level of free GGEL measured in a standard sample constituted by a pool of plasmas obtained from patients suffering from a disease associated with dysregulated apoptosis or from a population of healthy subjects.

In an embodiment of said method, monitoring apoptosis in said patient based on the comparison with the control is performed by:

(i) if the control is derived from a healthy subject or population of healthy subjects, determining that apoptosis is upregulated in the subject if the level of free GGEL in the plasma sample of the subject is greater than the level of free GGEL in the control, or determining that apoptosis is downregulated in the subject if the level of free GGEL in the plasma sample of the subject is lower than the level of free GGEL in the control; or (ii) if the control is derived from a subject or population of subjects suffering from disease associated with upregulated apoptosis, determining that apoptosis is upregulated in the subject if the level of free GGEL in the plasma sample of the subject is equal or greater than the level of free GGEL in the control; or (iii) if the control is derived from a subject or population of subjects suffering from disease associated with downregulated apoptosis, determining that apoptosis is downregulated in the subject if the level of free GGEL in the plasma sample of the subject is equal or lower than the level of free GGEL in the control.

The invention also relates to the use of monoclonal antibody specific for gamma-glutamyl-L-epsilon-Lysine (GGEL) according to the invention for the monitoring of apoptosis, in particular ex vivo monitoring of in vivo apoptosis.

The level of GGEL is measured by immunoassay, binding assay, or chromatography, as described previously.

Monitoring of apoptosis can be performed for, or enables for:
a) diagnosing a disease associated with dysregulated apoptosis, i.e. upregulated (enhanced) or downregulated (reduced) apoptosis, compared to a healthy subject; and
b) monitoring effectiveness of an apoptosis modulator treatment, i.e. apoptosis inducing treatment or apoptosis inhibiting treatment.

In particular, a method of diagnosis of a disease associated with upregulated apoptosis is provided, which comprises:
a) measuring the level of free gamma-glutamyl-L-epsilon-Lysine (GGEL) isopeptide in a plasma sample of the subject with the monoclonal antibody directed GGEL according to the invention;
b) comparing said measured level of free GGEL with a control; and
c) based on the comparison with the control, diagnosing that said subject suffers from a disease associated with upregulated apoptosis or not.

For diagnosis, if the control is derived from:
(i) a healthy subject or population of healthy subjects, it is diagnosed that said subject suffers from a disease associated with upregulated apoptosis if the level of free GGEL in the plasma sample of the subject is greater than the level of free GGEL in the control; or
(ii) a subject or population of subjects suffering from disease associated with upregulated apoptosis, it is diagnosed that said subject suffers from a disease associated with upregulated apoptosis if the level of free GGEL in the plasma sample of the subject is equal or greater than the level of free GGEL in the control.

A "disease associated with upregulated apoptosis" includes, without limitation:
neurodegenerative disorders, such as Alzheimer's disease, amyotrophic lateral sclerosis, Creutzfeld-Jakob's disease, Huntington's disease, Parkinson's disease, Retinitis pigmentosa, Spinal muscular atrophy, Cerebellar degeneration;
hematological disorders, such as Aplastic anemia, Fanconi anemia, Hodgkin's disease, Myelodysplastic syndromes, Polycythemia vera;
autoimmune disorders, such as Fulminant hepatitis, Graft-versus-host disease, Hashimoto's thyroiditis, Insulin-dependent diabetes mellitus, Multiple sclerosis, Rheumathoid arthritis, Scleroderma, Sjögren's syndrome;
ischemic injuries, such as Ischemia and reperfusion injury, Kidney infarction, Myocardial infarction, stroke;
toxin-induced diseases, such as Alcohol-induced hepatitis, Pulmonary fibrosisn sepsis;
bacterial or viral infections, such as infection with HIV (AIDS), hepatitis B or C virus, Ebola virus, *Chlamydia trachomatis, Helicobacter pylori, Neisseria meningitidis, Salmonella typhimurium, Shigella flexneri*;
or traumatic spinal cord injury, tumor counterattack (immune privilege).

In an embodiment, the disease associated with upregulated apoptosis is sepsis.

Actually, appoptosis of lymphocytes is a documented sign of sepsis and results in a decrease in B cells, CD4+ T cells, and follicular dendritic cells (Hotchkiss R S et al.; J Immunol 2001; 166; 6952-6963). As a consequence of this immunosuppression, antibody production, macrophage activation and antigen presentation are all decreased and are accompanied by the induction of tolerance to the infectious agent.

A method of diagnosis of a disease associated with downregulated apoptosis is also provided, which comprises:
a) measuring the level of free gamma-glutamyl-L-epsilon-Lysine (GGEL) isopeptide in a plasma sample of the subject with the monoclonal antibody directed GGEL according to the invention;
b) comparing said measured level of free GGEL with a control; and
c) based on the comparison with the control, diagnosing that said subject suffers from a disease associated with downregulated apoptosis or not.

For diagnosis, if the control is derived from:
(i) a healthy subject or population of healthy subjects, it is diagnosed that said subject suffers from a disease associated with downregulated apoptosis if the level of free GGEL in the plasma sample of the subject is lower than the level of free GGEL in the control; or
(ii) a subject or population of subjects suffering from disease associated with downregulated apoptosis, it is diagnosed that said subject suffers from a disease associated with downregulated apoptosis if the level of free GGEL in the plasma sample of the subject is equal or lower than the level of free GGEL in the control.

A "disease associated with downregulated apoptosis" includes, without limitation:
cancers, such as Blastoma, Carcinoma, Leukemia, Lymphoma, Malignant glioma, Sarcoma, Seminoma, breast cancer, prostate cancer, ovarian cancer;
premalignant diseases, such as Ataxia telangiectasia, Paroxysmal nocturnal hemoglobinuria, Myelodysplastic syndromes, Xeroderma pigmentosum;
autoimmune disorders, such as autoimmune lymphoproliferative syndrome (types I and II), Systemic lupus erythematosus, Immune-mediated glomerulonephritis; atherosclerosis;
metabolic disorders, such as Niemann-Pick's disease, Osteoporosis, Wilson's disease;
viral infections, such as infections with Adenovirus, Baculovirus, Epstein-Barr virus, Herpesvirus, Poxvirus;
premature aging, for instance Down's syndrome, Progeria, and Xeroderma pigmentosum.

Furthermore, the method of the invention provides accurate quantitation of the levels of the GGEL isopeptide which is directly correlated to the levels of apoptosis. Thus the effects of particular therapies or disease progression can be measured over time by testing for the appearance of the GGEL isopeptide (if the treatment is an apoptosis inducing treatment) or disappearance of the GGEL isopeptide (if the treatment is an apoptosis inhibiting treatment). During treatment, the level of GGEL isopeptide in the plasma is monitored over time to determine whether the level of apoptosis is increasing or decreasing in response to therapeutic treatment.

Accordingly, a method for monitoring effectiveness of an apoptosis inducing treatment in a subject is provided, which comprises:
a) measuring the level of free gamma-glutamyl-L-epsilon-Lysine (GGEL) isopeptide in a plasma sample of a subject undergoing an apoptosis inducing treatment, with a method according to the invention, in particular with an immunoassay using the monoclonal antibody according to any one of claims 1 to 3;
b) repeating the measurement of step a) in time; and
c) deducing that the apoptosis inducing treatment is effective if the level of free GGEL increases over time, or that the apoptosis inducing treatment is ineffective if the level of free GGEL is unchanged or decreases over time.

An apoptosis inducing treatment includes for instance:

agents inhibiting anti-apoptotic proteins such as Bcl-2, for instance oblimersen sodium (bcl-2 antisense), sodium butyrate, epispeptide, fenretinide, flavipirodo, gossypol, ABT-737 (CAS 852808-04-9), siRNA or antisense targeting Bcl-2;

p53 based gene therapy;

p53 based drug therapy, such as with Phikan083 (CAS 880813-36-5), CP-31398 dihydrochloride (CAS 1217195-61-3), nutlins such as nutlin-3 (CAS 548472-68-0);

agents inhibiting IAPS (inhibitor of apoptosis proteins: protein $BIRC_{1-8}$, survivin), such as siRNA or antisense targeting XIAP ($BIRC_4$);

caspase based drug therapy, such as apoptin.

Apoptosis inducers notably include Actinomycin, Apicidin, Bendamustine hydrochloride, Betulinic acid, Carboplatin, Cisplatin, Cyclophosphamide, Cladribine, Doxorubicin hydrochloride, Fludarabine, Gambogic acid, Kaempferol, 2-Methoxyestradiol, Mitomycin C, Piperlongumine, and Plumbagin.

Accordingly, a method for monitoring effectiveness of an apoptosis inhibiting treatment in a subject is provided, which comprises:

a) measuring the level of free gamma-glutamyl-L-epsilon-Lysine (GGEL) isopeptide in a plasma sample of a subject undergoing an apoptosis inhibiting treatment, with a method according to the invention, in particular with an immunoassay using the monoclonal antibody according to any one of claims 1 to 3;

b) repeating the measurement of step a) in time; and c) deducing that the apoptosis inhibiting treatment is effective if the level of free GGEL decreases over time, or that the apoptosis inhibiting treatment is ineffective if the level of free GGEL is unchanged or increases over time.

An apoptosis inhibiting treatment includes for instance c-Myc inhibitors, Bax-mediated apoptosis inhibitors, caspase inhibitors, Bongkrekic acid, CTP Inhibitors, Calpeptin (rho kinase inhibitor), Clofarabine (purine nucleoside antimetabolite), Combretastatin A4, Fasentin (inhibitor of glucose uptake that sensitizes cells to FAS-induced cell).

Method of Diagnosis and/or Monitoring of Sepsis

Sepsis is a syndrome associated with severe infection, typically pneumonia or gastrointestinal or urinary tract infection, and its successful treatment continues to represent a very important unmet clinical need. Sepsis is the leading cause of death in advanced countries accounting for the majority of deaths in Intensive Care Units (ICU) and hospitalised patients. In Europe, it affects around 750.000 patients annually (statistics in USA are similar) with a mortality rate around 40%. The cost to the health services is estimated between 15,000 to 20,000 euros/patient leading to an average annual cost of 10 billion euros.

A patient in ICU has a fever, a rapid heart rate, an elevated respiratory rate, or an abnormal white blood cell count. These symptoms could herald the onset of sepsis, a life-threatening systemic inflammatory response to infection, or they could be the result of trauma or a host of other conditions. Results from blood cultures have a high rate of false negatives—40 percent in one study (Vincent J. L., et al. Crit Care Med. 2006 February; 34(2):344-53)—and will not be available for up to 72 hours. The clock is ticking, and every hour of delayed treatment increases the likelihood of death (Kumar A. et al. Crit Care Med. 2006; 34(6):1593). Inappropriate antibiotic use can cause adverse side effects for the patient and encourage the development of drug-resistant bacteria.

The ability to diagnose sepsis rapidly and accurately, even in its early stages, remains one of the biggest challenges faced by clinical teams. Early diagnosis and treatment of suspected sepsis are essential to prevent life-threatening complications.

Sepsis diagnosis is currently difficult to establish because the manifestations of infection are very heterogenous. Due to this fact, in 1992, the international conference on sepsis, including the ACCP (American College of Chest Physicians) and the SCCM (Society of Critical Care Medicine) defined sepsis as a "Systemic Inflammatory Response Syndrome (SIRS) to an infection" (Bone R C.; JAMA. 1992 Dec. 23-30; 268(24):3452-5; Levy M M et al.; SCCM/ESICM/ACCP/ATS/SIS.; Crit Care Med. 2003 April; 31(4): 1250). To further facilitate patient evaluation, the pathology was differentiated into several stages:

the SIRS, corresponding to an inflammatory response;

the sepsis, defined as life-threatening organ dysfunction caused by a dysregulated host response to infection;

the septic shock, defined as a subset of sepsis in which particularly profound circulatory, cellular, and metabolic abnormalities are associated with a greater risk of mortality than with sepsis alone.

The gold standard of sepsis diagnosis has traditionally been the use of microbial cultures to identify the source of illness. But, the major limitation of using cultures is the length of time required to develop cultures to identifiable quantities. Cultures are also reported to be insensitive under several conditions, including slow-growing and no cultivatable microorganisms and microorganisms present at very low concentrations. In light of these disadvantages, alternative diagnostic methods using molecular-based tests have been developed to enable rapid and/or automated diagnosis of sepsis. These tests include ELISA kits, flow cytometry, immunoluminometric assays, PCR tests, automated microbiological systems and FISH techniques, which are all aimed at detecting the main responsible bacteria for sepsis.

Prognostic scoring systems can facilitate quality assessment of the ICU by allowing comparison of its overall performance to a large-scale representative database. The 3 commonly used scoring systems are Acute Physiology and Chronic Health Evaluation (APACHE), Simplified Acute Physiology Score (SAPS) and Mortality Probability Model (MPM). A recent study showed that Predicted Mortality of APACHE-IV and SAPS-II Scoring Systems did not correlate with the observed mortality for patients with severe sepsis and septic shock (Dabhi A S, Khedekar S S, Mehalingam V; J Clin Diagn Res. 2014 October; 8(10):MCO9-13).

In parallel to the development of faster and more sensitive detection methods of infectious microbes is the development of systems monitoring abnormal changes in specific serum protein biomarker concentrations. A biomarker is best defined as a characteristic that is objectively measured and evaluated as an indicator of normal biologic or pathogenic processes. Hundreds of biomarkers have been studied in an attempt to identify a reliable marker able to fulfil the need for quicker, more specific and more accurate diagnosis of sepsis.

Studies on the mechanism of sepsis identified 178 potential biomarkers (Pierrakos C, Vincent J L; Critical care; 2010; 14:R15). These biomarkers were classified into four categories: biomarkers of infection, biomarkers of inflammation, biomarkers of haemostasis and biomarkers of apoptosis. These biomarkers can help to differentiate patients with SIRS from those with sepsis (such as Procalcitonin, CD64, or s-TREM-1). However, even these markers do not permit an exact classification of the patient and must be used in conjunction with the existing protocol for Procalcitonin positive patients (Kim H S et al.; Ann Clin Lab Sci. 2012 Winter; 42(1):57-64) or C-reactive protein.

A study on inflammation markers showed that the initial pro-inflammatory response is followed by an immunodepressive phase that provides evidence for several defects in the immune response in the evolution of sepsis (Wesche D E et al.; J Leukoc Biol.; 2005 August; 78(2):325-37). Indeed, the inflammatory response of the host is an equilibrium between pro-inflammatory (SIRS) and anti-inflammatory mediators (CARS). Among the mediators of SIRS are tumour necrosis factor (TNF) and the pro-inflammatory cytokines, whilst among the mediators of CARS are the antagonists of the IL1 receptor and IL10. During the development of septic shock, the controlled expression of the mediators of SIRS and CARS is perturbed thereby leading to an excessive pro-inflammatory response.

Although these markers may be used to monitor the development of sepsis, they are not specific or sensitive enough to reliably distinguish early sepsis from late sepsis and the inception of severe sepsis.

The invention aims at providing methods, tools and kits for sepsis detection, in particular for early sepsis detection, enabling a quick and reliable detection of biomarkers for sorting patients, but also for monitoring sepsis evolution towards severe sepsis.

The inventors have shown that free gamma-glutamyl-L-epsilon-Lysine (GGEL) is an effective biomarker of sepsis, and in particular of early sepsis.

In the case of suspected sepsis, it is important to get a diagnosis as soon as possible so that appropriate treatment can be given. This can help stop the progression of sepsis and reduce the risk of long-term damage to the body, or death, as far as nowadays, the average lifetime is estimated up to 28 days once treatment starts when sepsis is identified.

"Sepsis" is a systemic response to a localized but serious infection, which is usually bacterial in origin but may be of fungal, viral or parasitic source. *Staphylococcus aureus* and *Streptococcus pneumoniae* are the most common gram-positive isolates, whereas *Escherichia coli*, *Klebsiella species*, and *Pseudomonas aeruginosa* predominate among gram-negative isolates. Endotoxin is released from replicating or dying gram-negative bacteria in the blood streams, and thus initiates the inflammatory cascade of sepsis.

Sepsis and septic shock are defined as detailed in Table 1.

TABLE 1

Summary of Third International Consensus Definitions for Sepsis and Septic Shock

| | Definition | Clinical Operationalization |
| --- | --- | --- |
| Sepsis | Life-threatening organ dysfunction caused by a dysregulated host response to infection. | Organ dysfunction can be represented by an increase in the Sequential Organ Failure Assessment (see Table 2) score of 2 points or more, which is associated with an in-hospital mortality greater than 10%. |
| Septic Shock | A subset of sepsis in which particularly profound circulatory, cellular, and metabolic abnormalities are associated with a greater risk of mortality than with sepsis alone. | Identified by a vasopressor requirement to maintain a mean arterial pressure of 65 mm Hg or greater AND serum lactate level greater than 2 mmol/L in the absence of hypovolemia. |

TABLE 2

Sequential (Sepsis-Related) Organ Failure Assessment Score (SOFA)

| | Score | | | | |
| --- | --- | --- | --- | --- | --- |
| System | 0 | 1 | 2 | 3 | 4 |
| Respiration | | | | | |
| $PaO_2/FIO_2$ mm Hg | ≥400 (53.3) | <400 (53.3) | <300 (40) | <200 (26.7) with respiratory support | <100 (13.3) with respiratory support |
| Coagulation | | | | | |
| Platelets, $\times 10^3$/μL | ≥150 | <150 | <100 | <50 | <20 |
| Liver | | | | | |
| Bilirubin, mg/dL (μmol/L) | <1.2 (20) | 1.2-1.9 (20-32) | 2.0-5.9 (33-101) | 6.0-11.9 (102-204) | >12.0 (204) |
| Cardiovascular | MAP ≥70 mm Hg | MAP <70 mm Hg | Dopamine <5 or dobutamine (any dose)[b] | Dopamine 5.1-15 or epinephrine ≤0.1 or norepinephrine ≤0.1[b] | Dopamine >15 or epinephrine >0.1 or norepinephrine >0.1[b] |
| Central nervous system | | | | | |
| Glasgow Coma Scale score[c] | 15 | 13-14 | 10-12 | 6-9 | <6 |

TABLE 2-continued

Sequential (Sepsis-Related) Organ Failure Assessment Score (SOFA)

| | Score | | | | |
|---|---|---|---|---|---|
| System | 0 | 1 | 2 | 3 | 4 |
| | Renal | | | | |
| Creatinine, mg/dl (μmol/l) | <1.2 (110) | 1.2-1.9 (110-170) | 2.0-3.4 (171-299) | 3.5-4.9 (300-440) | >5.0 (440) |
| Urine output, ml/dl | | | | <500 | <200 |

Abbreviations: $FIO_2$, fraction of inspired oxygen; MAP, mean arterial pressure; $PaO_2$, partial pressure of oxygen.
[b]Catecholamine doses are given as μg/kg/min for at least 1 hour
[c]Glasgow Coma Scale scores range from 3-15; higher score indicates better neurological function As used herein "early sepsis" denotes the sepsis phase ranging from day 0 to day 3 from sepsis onset, and in a preferred embodiment from day 0 to day 1 from sepsis onset.

According to an embodiment, the invention relates to an ex vivo method for the diagnosis of sepsis in a subject, which comprises:
  a) measuring the level of free gamma-glutamyl-L-epsilon-Lysine (GGEL) isopeptide in a plasma sample of the subject;
  b) comparing said measured level of free GGEL with a control; and
  c) determining if said subject suffers from sepsis based on the comparison with the control.

Said method relies on the detection of free GGEL released in the circulation following apoptosis of cells induced in the early stage of sepsis.

In particular, the method advantageously makes it possible to diagnose early sepsis.

The control may be a single value or a range of values, which is determined, based on the level of free GGEL in plasma samples from a subject or population of healthy subjects, or from a subject or population of subjects suffering from sepsis. Typically, the analysed population can be divided into quantiles based on the measured level of free GGEL. The control can be defined as the median, or the second tertile, or the second or third quartile, or the third or fourth quintile etc. . . . . The control can also be defined as the mean free GGEL level in plasma samples from a subject or population of healthy subjects, or from a subject or population of subjects suffering from sepsis, preferably early sepsis.

The control can also be determined by analysing a plasma sample from the same subject at an earlier time point, for instance prior to onset of sepsis or prior to suspicion of sepsis.

Comparison with a control may also be performed by comparing the measured level of free GGEL with the level of free GGEL measured in a standard sample constituted by a pool of plasmas obtained from patients having sepsis or from a population of healthy subjects.

In an embodiment determining that said patient suffers from sepsis based on the comparison with the control is performed by:
  (i) if the control is derived from a healthy subject or population of healthy subjects, determining that the subject suffers from sepsis if the level of free GGEL in the plasma sample of the subject is greater than the level of free GGEL in the control; or
  (ii) if the control is derived from a subject or population of subjects suffering from sepsis, determining that the subject suffers from sepsis if the level of free GGEL in the plasma sample of the subject is equal or greater than the level of free GGEL in the control.

Preferably, when the control is derived from a subject or population of subjects suffering from sepsis, the control is derived from a subject or population suffering from early sepsis, and preferably from a sepsis within the first day following onset.

A subject diagnosed with sepsis by measurement of the level of free GGEL isopeptide according to the method of the invention can be further monitored for a possible evolution towards severe sepsis by an ex vivo method for monitoring evolution of sepsis towards severe sepsis as described hereafter.

The marker diagnostic performance can be characterised by sensitivity, which represents its ability to detect the sepsis population, and specificity, which represents its ability to detect the control population.

The results of the evaluation of a diagnostic test can be summarised in a 2×2 contingency table comparing these two well-defined populations. By fixing a cut-off, the two populations can be classified into categories according to the results of the test, categorised as either positive or negative. Given a particular marker, a number of subjects can be identified with a positive test result among the "cases" population (the "True Positive": TP) and b subjects with a positive test result among the "controls" population (the "True Negative": TN). In the same fashion, c subjects with a negative test result among the cases (the "False Positive": FP) and d subjects with a negative test result among the controls (the "False Negative": FN) are observed. Sensitivity is defined as TP/(TP+FN); which is herein referred to as the "true positive rate". Specificity is defined as TN/(TN+FP); which is herein referred to as the "true negative rate".

As reported in Table 6 of the following example 4, specificity of free GGEL quantitation was evaluated to 91% for sepsis diagnosis at day 1 from onset, to 100% for sepsis diagnosis at day 3 from onset, and to 95.45% for sepsis diagnosis from day 1 to day 3 from onset.

Figure 5:
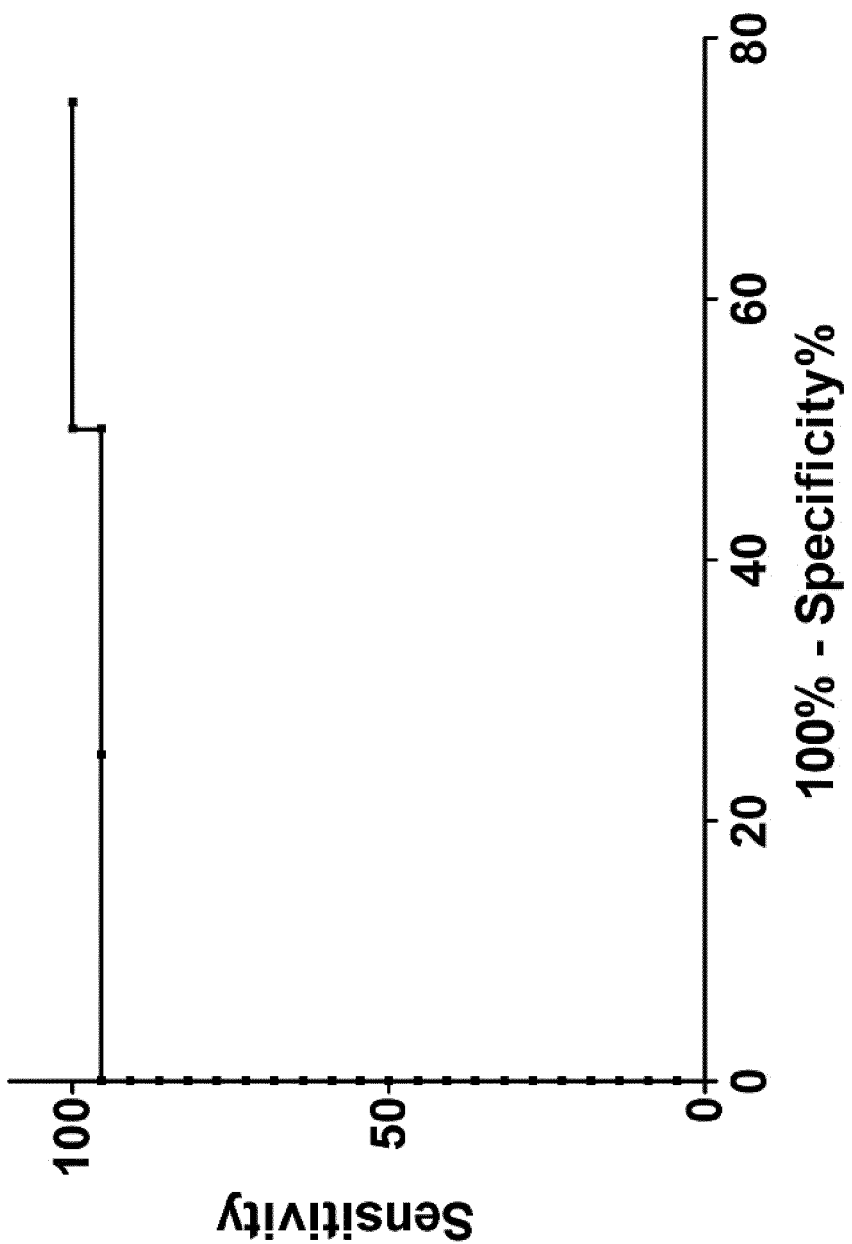

The accuracy of free GGEL and its discriminatory power was also evaluated using a Receiving Operating Characteristics (ROC) analysis (see FIG. 5 and Table 7). ROC curves are the graphical visualization of the reciprocal relation between the sensitivity (Se) and the specificity (Sp) of a test for various values.

mROC is a program developed by Kramar et al. (Comput Methods Programs Biomed, 2001, 66:199-207) which is dedicated to identify the linear combination which maximizes the AUC (Area Under the Curve) of ROC curves. The use of this program was described for instance in Staack et al. BMC Urol 2006; 6:19. This program implements an algorithm for maximising rank correlation estimation which is also an estimate for the area under the ROC curve (Su and Liu. Journal of the American Statistical Association 1993; 88:1350-1355; Wang, Computational Statistics and Data Analysis 2007; 51:2803-2812).

A ROC curve is a graphical representation of the sensitivity (or true positive rate) against the false positive rate (i.e. [1−specificity], specificity being the true negative rate) of a marker-based test. A ROC space is defined by sensitivity and (1−specificity) as x and y axes respectively. The best possible prediction method would yield a point in the upper left corner or coordinate (0,1) of the ROC space, representing 100% sensitivity (no false negatives) and 100% specificity (no false positives). A completely random guess would give a point along a diagonal line (the so-called line of no-discrimination) from the left bottom to the top right corners. The diagonal divides the ROC space. Points above the diagonal represent good classification results (better than random), points below the line poor results (worse than random). The Area Under the Curve (AUC) of a ROC curve may be calculated. The higher the AUC, the higher the diagnostic accuracy of the diagnostic marker.

The invention further relates to the use of a ligand directed to GGEL, or specific to GGEL, for the diagnostic and/or monitoring of sepsis.

In an embodiment, said ligand is used for diagnosing early sepsis. In said use, the ligand is employed in order to measure free GGEL.

Lateral Flow Immunoassay Device

The invention further relates to a lateral flow immunoassay device which comprises a monoclonal antibody specific for GGEL, which comprises CDR-H1 of sequence GYTFTSY (SEQ ID NO:3), CDR-H2 of sequence NPSNGG (SEQ ID NO:4), CDR-H3 of sequence SGLLL-WSPWFAY (SEQ ID NO:5), CDR-L1 of sequence RASENIYSYLA (SEQ ID NO:6), CDR-L2 of sequence NAKTLAE (SEQ ID NO:7), and CDR-L3 of sequence QHHYGTPFT (SEQ ID NO:8), according to the invention.

The lateral flow immunoassay device comprises a test strip 1 comprising a detection zone 2 wherein the detection zone comprises a test region 3 containing immobilized thereon said monoclonal antibodies specific for GGEL, and a control region 4.

The test strip supports lateral flow of a fluid along a lateral flow direction, the one or more test regions and one or more control regions include an area that is exposed for optical or visual inspection. The test strip is typically a membrane, in particular a porous membrane.

A lateral flow immunoassay device usually further includes an absorbent pad 5 (positioned at the top of the test strip (or membrane) to increase the volume of the flowing liquid), a sample port 7 and a sample pad 6 (to assure contact between the liquid sample to be assayed and the test strip (or membrane)), and a rigid backing (housing 8).

In an embodiment, the lateral flow immunoassay device is designed as an indirect competitive LFIAs. Indirect competitive LFIAs, which exploit gold-labelled antibodies, have been widely described.

In this embodiment, the lateral flow immunoassay device further includes a conjugate pad 9 comprising gold-labelled anti-GGEL specific antibodies and gold-labelled non-specific immunoglobulins (in particular IgG).

The gold-labelled anti-GGEL specific antibody is suspended in the liquid sample and flows through the membrane where it first encounters the GGEL antigen (for instance as BSA-GGEL) coated in the "Test Line" 10. In the absence of the GGEL target compound in the sample to be assayed, gold-labelled anti-GGEL specific antibodies bind to the coated GGEL antigen and are focused on the "Test Line", so that a visible band is formed. A second "Control Line" 11 follows and is constituted of a secondary anti-species antibody (non-specific γ-globulins) which captures any excess of anti-GGEL specific antibodies. The appearance of the "Control Line" can be considered as the confirmation of the good migration of the liquid through the membrane. When the GGEL target compound is present in the sample to be assayed above the lower detectable concentration level, binding of gold-labelled anti-GGEL specific antibodies to the coated GGEL antigen in the Test Line is inhibited, due to the initial interaction of the anti-GGEL specific antibodies with GGEL present in the sample, resulting in a non-visible "Test Line".

Interpretation of assay results depends on the presence and intensity of both Test and Control Lines: two intense lines indicate that the test is valid, and the sample is negative (i.e. GGEL in the sample um is below the detection limit of the method); intense Control Line and fading Test Line indicate that the test is valid, and the amount of the GGEL in the sample is near to the detection limit; intense Control Line indicate that the is valid and the sample positive (the amount of the GGEL in the sample is above the detection limit); intense or fading Test Line indicate that the test is invalid.

Methods of Treatment

The invention relates also to a method of treating a disease associated with dysregulated apoptosis in a subject in need thereof, which comprises:
 a) administering an apoptosis modulating treatment to a subject treating suffering from a disease associated with dysregulated apoptosis
 b) monitoring if said treatment modulates apoptosis in the subject by implementing the method of monitoring of apoptosis according to the invention; and
 c) continuing or modifying the apoptosis modulating treatment based on the result of monitoring of step b).

In an embodiment, the invention relates also to a method of treating a disease associated with upregulated apoptosis in a subject in need thereof, which comprises:
 a) administering an apoptosis inhibiting treatment to a subject treating suffering from a disease associated with upregulated apoptosis
 b) monitoring if said treatment inhibits apoptosis in the subject by implementing the method of monitoring of apoptosis according to the invention; and
 c) continuing the apoptosis inhibiting treatment if the result of monitoring of step b) indicates that the treatment inhibits apoptosis in the subject, or modifying treatment if the result of monitoring of step b) indicates that the treatment does not inhibit apoptosis in the subject.

In an embodiment, the invention relates also to a method of treating a disease associated with downregulated apoptosis in a subject in need thereof, which comprises:
 a) administering an apoptosis inducing treatment to a subject treating suffering from a disease associated with downregulated apoptosis
 b) monitoring if said treatment induces apoptosis in the subject by implementing the method of monitoring of apoptosis according to the invention; and
 c) continuing the apoptosis inducing treatment if the result of monitoring of step b) indicates that the treatment induces apoptosis in the subject, or modifying treatment if the result of monitoring of step b) indicates that the treatment does not induce apoptosis in the subject.

The invention further relates to a method of treating sepsis in a subject in need thereof, which comprises:
  a) diagnosing sepsis in a subject suspected of having sepsis, by a method of diagnostic of sepsis of the invention, i.e. a method which comprises:
    i. measuring the level of free gamma-glutamyl-L-epsilon-Lysine (GGEL) isopeptide in a plasma sample of the subject;
    ii. comparing said measured level of GGEL with a control; and
    iii. determining if said subject suffers from sepsis based on the comparison with the control; and
  b) administering a therapeutic treatment against sepsis to the subject diagnosed as suffering from sepsis.

The invention also relates to a method of treating sepsis in a subject in need thereof, which comprises administering a therapeutic treatment against sepsis to a subject known to suffer from sepsis based on measurement of free gamma-glutamyl-L-epsilon-Lysine (GGEL) isopeptide in a plasma sample of said subject.

The invention also relates to a therapeutic treatment against sepsis for use for treating sepsis in subject, wherein the subject is known to suffer from sepsis based on measurement of free gamma-glutamyl-L-epsilon-Lysine (GGEL) isopeptide in a plasma sample of said subject.

In an embodiment, said subject known to suffer from sepsis based on measurement of free gamma-glutamyl-L-epsilon-Lysine (GGEL) isopeptide in a plasma sample of said subject, has been previously diagnosed by the ex vivo method for the diagnostic of sepsis according to the invention.

Accordingly, the invention also relates to a therapeutic treatment against sepsis for use for treating sepsis in subject, comprising diagnosing sepsis by the method of the invention.

A therapeutic treatment against sepsis includes administering broad-spectrum antibiotics (i.e. antibiotics having activity against both gram-positive and gram-negative bacteria), preferably as soon as possible once sepsis has been diagnosed. Broad-spectrum antibiotics include for instance streptomycin, ampicilllin, tetracyclines, phenicols, fluoroquinolones, "third-generation" and "fourth-generation" cephalosporins.

Antibiotic choice typically depends on the probable source of infection, local policy, and may involve selection of appropriate antibiotic after microbiological analysis. Antibiotic therapy may be reviewed daily to reduce toxicity, and risk of resistance.

If sepsis is determined to evolve towards severe sepsis, sepsis treatment is to be modified by changing antibiotic if resistance to treatment is suspected, and/or placing the subject under more invasive monitoring and treatment.

Kits

The invention also relates to a kit for the monitoring of apoptosis which comprises:
  a) a monoclonal antibody specific for gamma-glutamyl-L-epsilon-Lysine (GGEL) according to the invention; and
  b) a control.

The invention relates in particular to a kit for the diagnostic and/or monitoring of sepsis which comprises:
  a) a monoclonal antibody specific for gamma-glutamyl-L-epsilon-Lysine (GGEL) according to the invention; and
  b) a control.

If the kit is for the diagnostic of sepsis, the kit then includes at least a control of free GGEL level. The control may be a single value or a range of values which is determined based on the level of free GGEL in plasma samples from a subject or population of healthy subjects, or from a subject or population of subjects suffering from sepsis, preferably early sepsis. Typically, the analysed population can be divided into quantiles based on the measured level of free GGEL. The control can be defined as the median, or the second tertile, or the second or third quartile, or the third or fourth quintile etc. . . . . The control can also be defined as the mean free GGEL level in plasma samples from a subject or population of healthy subjects, or from a subject or population of subjects suffering from sepsis, preferably early sepsis. The control may also be a pool of plasmas obtained from patients having sepsis, preferably early sepsis, or from a population of According to an embodiment, the constituents of the kit are adsorbed on a lateral flow immunoassay device.

According to another embodiment, the kit further comprises red blood cells (RBC) and GGEL. Preferably, said kit comprises GGEL coated on RBC and said monoclonal antibody specific for GGEL according to the invention. Such a kit is suitable to implement a GGEL immunoassay in Coomb's assay format.

The invention will be further illustrated in view of the following figures and examples.

FIGURES

FIG. 1. Formation of N-ε-(γ-glutamyl)-L-lysine isopeptide bond by transglutaminase reaction.

Figure 2:
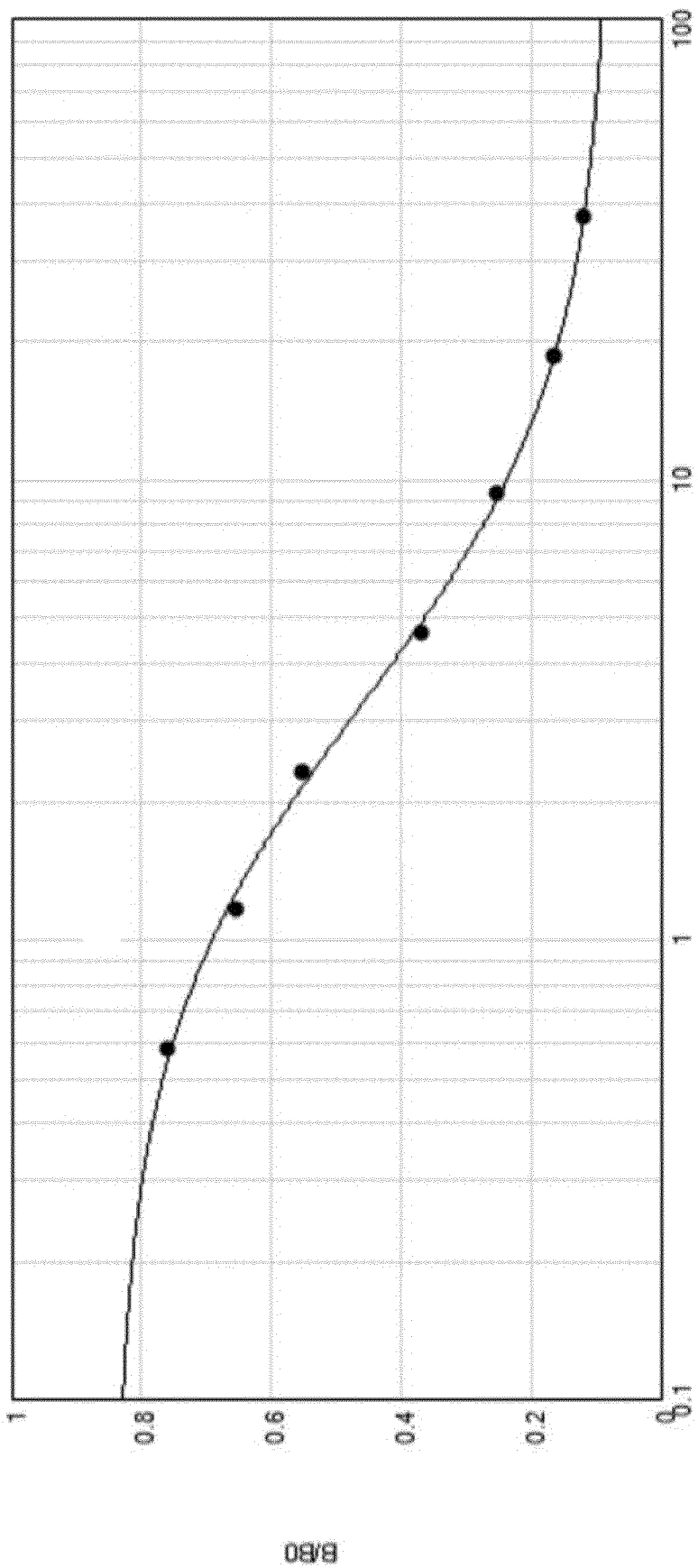

FIG. 2. Quantification of GGEL concentration using standard curve. Standardized BZGO with known amount of GGEL were used as standard for the quantification of GGEL. Standard curve was calculated using 4-Parameter line using SoftMax Pro 6.5.

Figure 3:
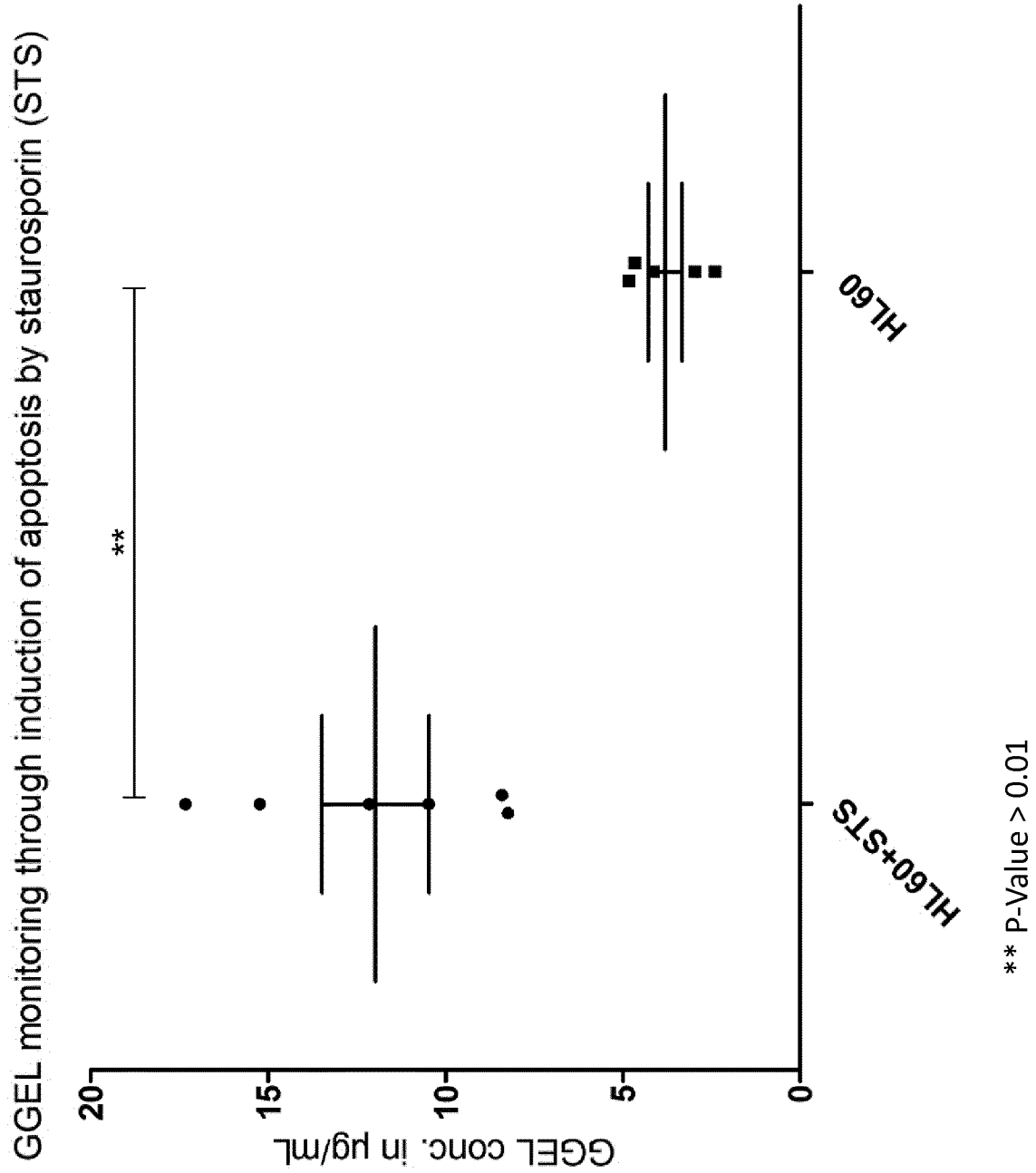

FIG. 3. GGEL quantification after induction of apoptosis by staurosporin 1 μmol/L (STS) in HL60 cells. GGEL concentration in apoptosis-induced cell group was significantly different from GGEL concentration in cell group non-induced into apoptosis. (P value<0.05).

Figure 4:
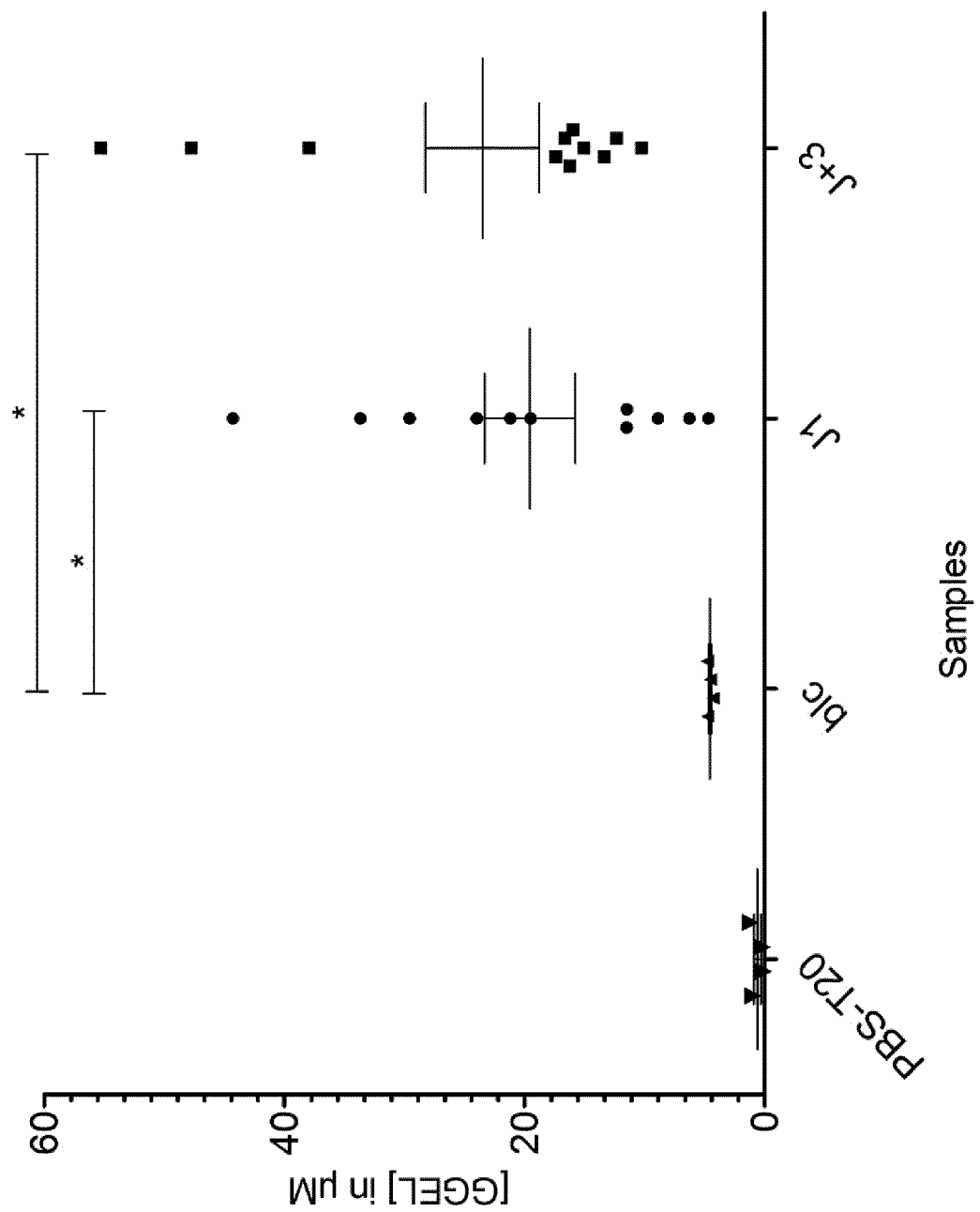

FIG. 4. Results of GGEL quantification in sepsis plasma (PBS-T20: Phosphate Buffer Saline with Tween 20=negative control, Blank plasma=control plasma, Plasma sepsis D1=plasma from sepsis patient at day+1, Plasma sepsis D3=plasma from sepsis patient at day+3).

FIG. 5. Blank plasma were used in order to determinate the threshold of the test (V=μ×3 SD). Specificity and sensitivity data were obtained resulting in a specificity of 91% for D1 group, 100% for D+3 group and 95.45% for the merged group (D1+D+3). ROC curve of the test was obtained. All plasma have been diluted at 1/20.

Figure 6:
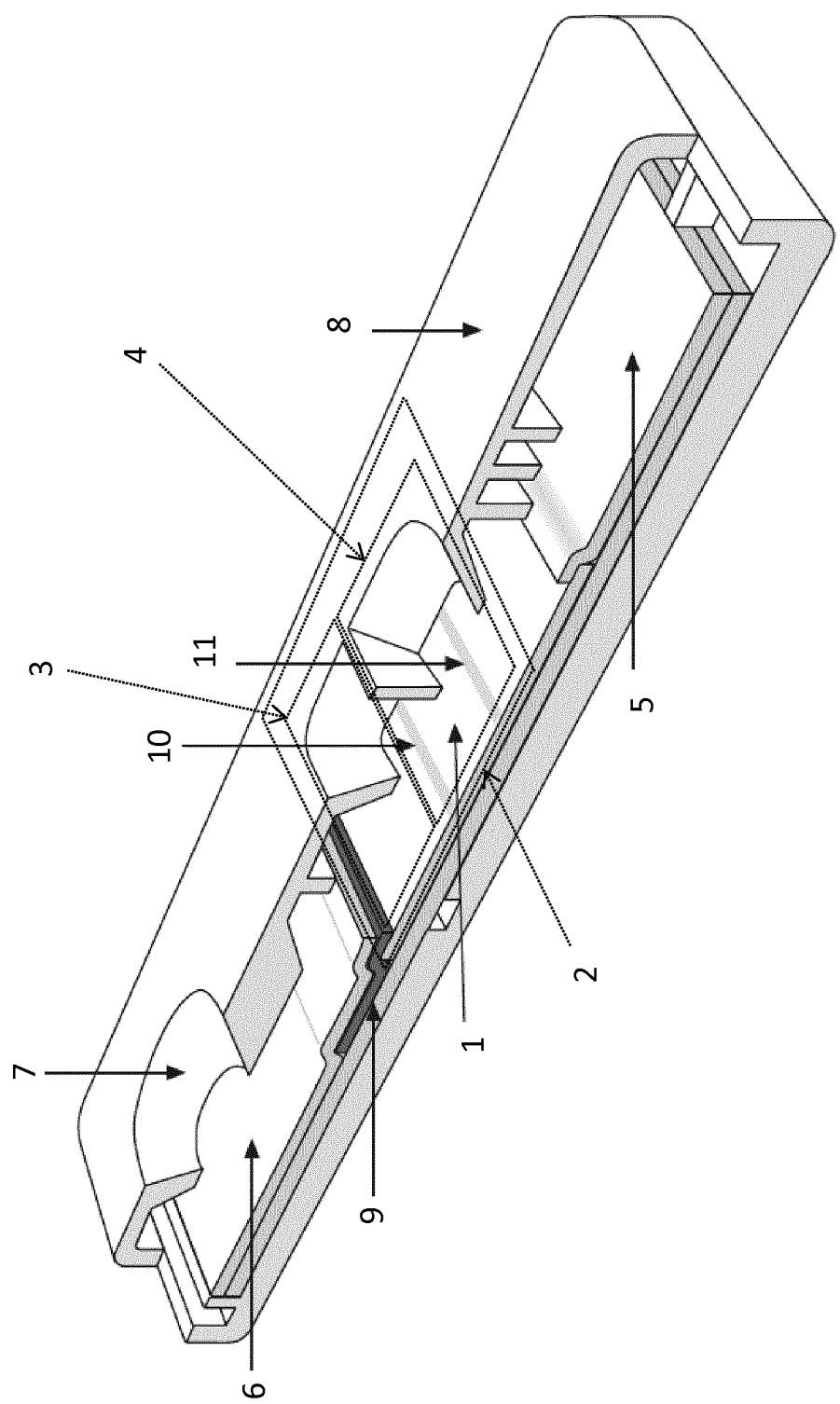

FIG. 6. Exemplary lateral flow immunoassay device.

Figure 7:
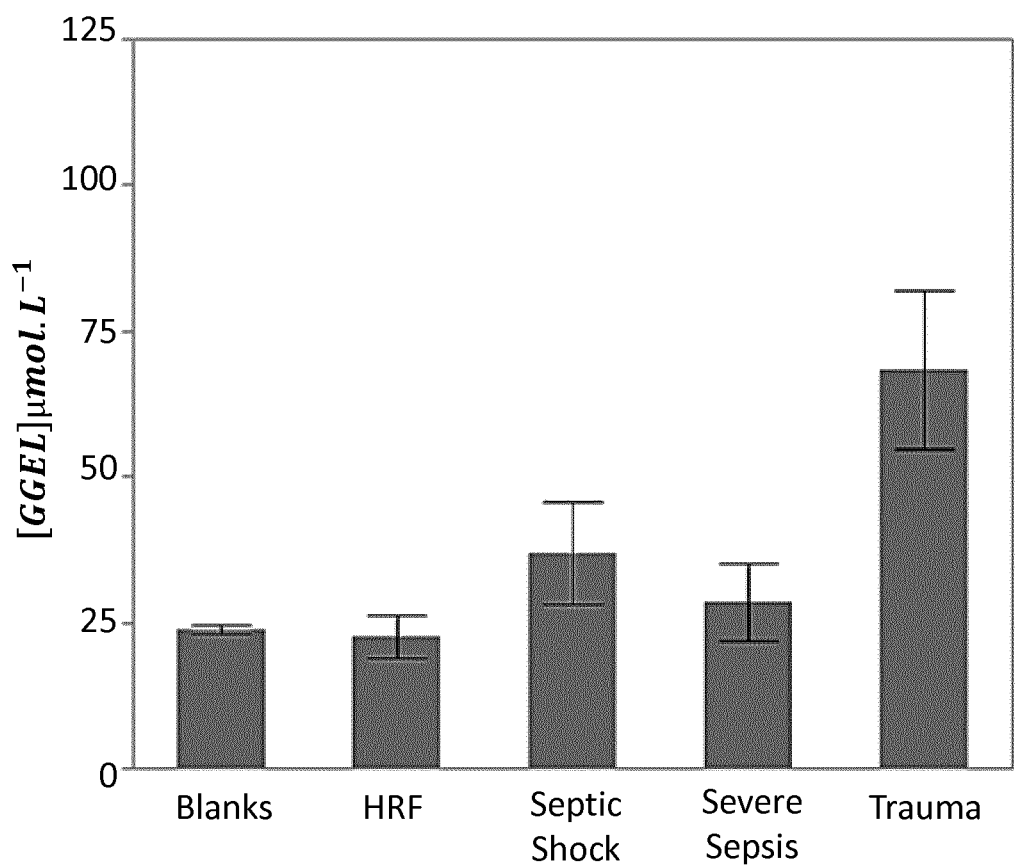

FIG. 7. GGEL quantification between different pathologies.

Figure 8:
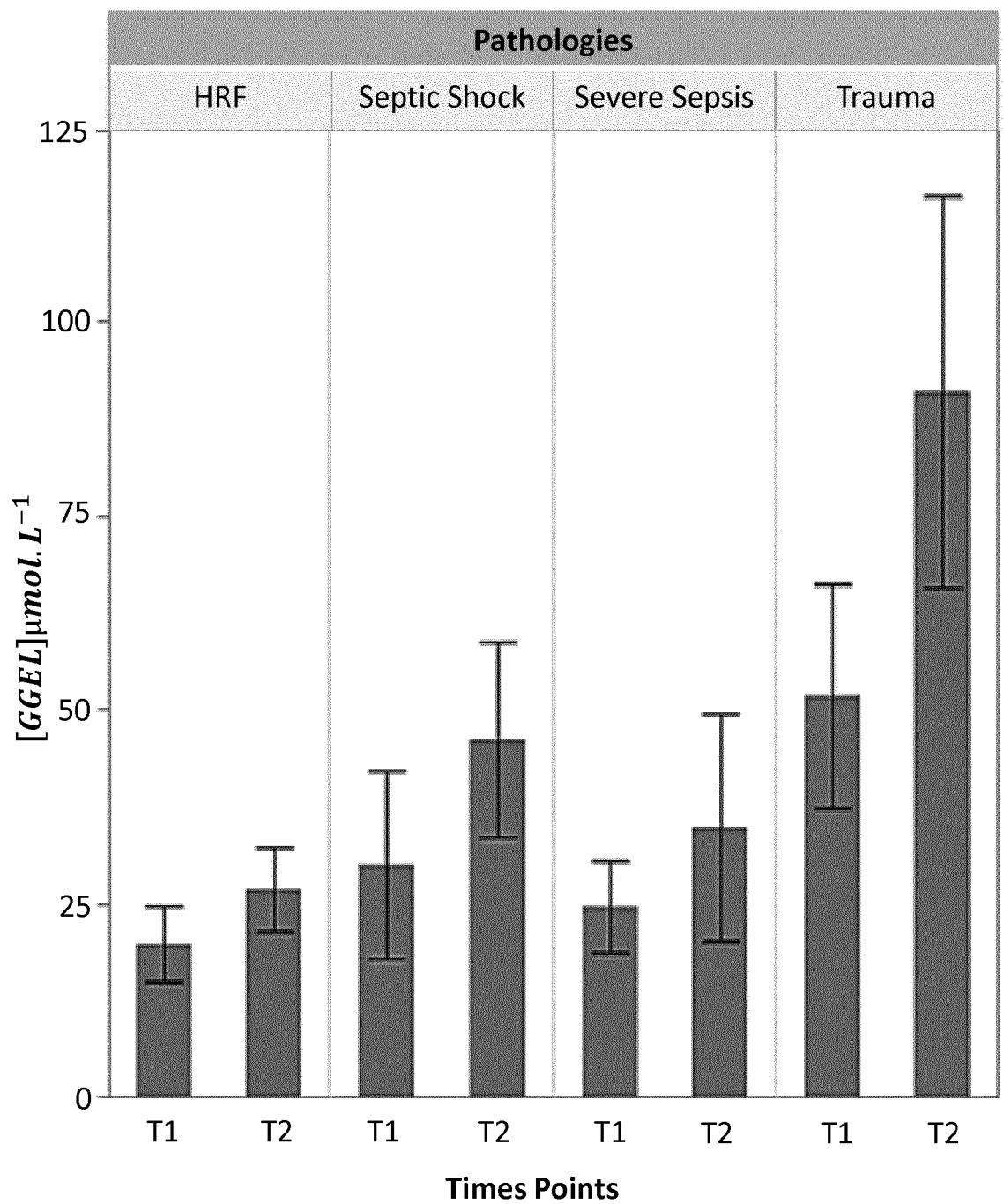

FIG. 8. GGEL plasma concentration between time points T1 and T2 in different pathologies.

EXAMPLE

Example 1: Development of a Monoclonal Antibody Specific to Gamma-Glutamyl-L-Epsilon-Lysine (GGEL)

Materials & Methods

Development of mAb, Preparation of Immunogen and Immunization Regime.

Mice were immunized with gamma-glutamyl-L-epsilon-Lysine (GGEL) coupled on Keyhole limpet hemocyanin (KLH) via glutaraldehyde and then dialysed against Phosphate Buffer Saline 1×(PBS).

25 µg of antigenic solution was dissolve in 100 µL of PBS. Six-weeks-old BALB/c and SJL female white mice were given four intranodal injection of immunogen at 1 week intervals and a single intraperitoneal injection three days before fusion.

Production and Screening of Hybridomas.

Hybridoma cells were produced by the method described elsewhere Galfre and Milstein (1981). The supernatant were screened by enzyme-linked immunosorbent assay (ELISA) against GGEL coupled to bovine Serum Albumine (BSA) immobilized to the wells of Maxisorp microtiter plates. Wells containing immobilized antigens were incubated with hybridomas supernatant for 1 h, followed with goat anti-mouse (H+L) peroxidase conjugate diluted 1 in 2000 in PBS containing Tween 20 0.05% (PBST) for one hour. Bound antibody was visualized by incubating wells with tetramethyl benzidine substrate (TMB) for five minutes and reaction were stopped with $H_2SO_4$, 2N. Absorbance values were determined at 450 nm with Spectramax i3® automated microplate reader (Molecular Devices, Sunnydale, USA). Wells were given four rinses with PBST between each incubations. Working volumes were 100 µL per well, and control wells were incubated with culture medium. All incubation were performed at 37° C. Threshold for detection of antibody in ELISA were determined from negative control means.

Determination of Ig Subclass and Cloning Procedure.

The Ig class of mAbs was determined with a commercial mouse mAb isotyping kit (ISO-1) according to the manufacturer's instructions (Sigma). All antibody that was developed for this project have been IgM. Hybridoma cells lines were cloned by limiting dilution, and cell lines Were grown in bulk in a non-selective medium, preserved by slowly freezing in fetal bovine serum/dimethyl sulfoxide (92:8 [vol/vol]), and stored in liquid nitrogen.

Antibody Precipitation.

Selected hybridomas were cultivated in RPMI-1640 supplemented of Fecal Calf Serum (FCS) 10%. After 2-weeks cultivation in incubator 37° C., 5% CO2 and 95% of humidity, supernatant were dialysis against water in order to precipitate IgM three times. After centrifugation of 2000 g 30 minutes at +4° C., pellet were resuspended in phosphate buffer 20 mM pH8.00 supplemented with 1 M NaCl. Then dialysis against PBS three times. Concentrations of precipitated antibody were calculated using absorbance at 280 nm with Spectradrop® automated microplate reader (Molecular Devices, Sunnydale, USA).

Antibody Specificity Determination. Synthesis of Antigenic Protein.

For specificity validation of each selected hybridoma, antigenic proteins that mimic the isopeptide (GGEL) were synthetized:

GGEL were coupled on bovine serum albumin (BSA) using glutaraldehyde as crosslinking agent (GGEL-BSA). To that end, a solution of GGEL/NaOH 1 M 0.36 mg/ml, 151 nM of BSA and 2.5% of glutaraldehyde (10 mg/ml) were mixed and incubated overnight. Dialysis was performed against PBS three times.

N-Alpha-Cbz-L-Lysine Methyl Ester (Z-GluOme) were coupled to BSA (BZGO) using (EDC) and N-hydroxysuccinimide (NHS) as crosslinking agent (LysOMe-BSA). N-alpha-Cbz-Glutamic acid Methyl Ester coupled to BSA (BZGO); GGEL isopeptide bounds were created between Z-GluOme and BSA lysines' using N-(3-Dimethylaminopropyl)-N'-ethylcarbodiimide hydrochloride (EDC) and NHS. EDC 490 µmol/L/ NHS 524 µmol/L and Z-GluOme 295 mmol/L were diluted in dimethylformamide (DMF) and incubated 15 min at room temperature. BSA 2 mg/ml diluted in a 0.1 M phosphate buffer pH 8.00 was added and incubated overnight. Dialysis was performed against PBS, three times.

N-alpha-Cbz-Glutamic acid-Tert-Butyl Ester coupled to BSA (GluOter-BSA); GGEL isopeptide bounds were created between Z-GluOter and BSA lysines' using N-(3-Dimethylaminopropyl)-N'-ethylcarbodiimide hydrochloride (EDC) and NHS. EDC 490 µmol/L/NHS 524 µmol/L and Z-GluOter 295 mmol/L were diluted in dimethylformamide (DMF) and incubated 15 min at room temperature. BSA 2 mg/ml diluted in a 0.1 M phosphate buffer pH 8.00 was added and incubated overnight. Dialysis was performed against PBS, three times.

Antigenic proteins that mimic unwanted isopeptide (alpha-Glycine-L-espilon-Lysine, ubiquitin isopeptide), acetylation of Lysine or polyamine crosslink were synthetized:

N-Alpha-Boc-Glycine were coupled to BSA using EDC and NHS as coupling agent (Boc-Gly-BSA), Spermidine was coupled to poly-L-Glutamic using EDC/ NHS (Spd-pGlu), BSA was treated with anhydride acetic to for acetylation on primary amine of the protein (Lysine) (BSA-Ac).

In order to evaluate the quantity of GGEL isopeptide created on BSA, a quantification of primary amine with 2,4,6-trinitrobenzene sulfonic acid (TNBS) test was performed. Proteins were diluted at 100 µg/mL in a 0.1 mol/L bicarbonate solution supplemented with 0.01% TNBS. After 2 h of incubation at 37° C., reaction was stopped with hydrogen chloride (HCl) 1N. Optical densities were read at 335 nm with Spectramax i3® automated microplate reader (Molecular Devices, Sunnydale, USA).

TABLE 2

Antigenic proteins used for specificity determination that mimic GGEL isopeptide.

| | |
|---|---|
| GGEL on protein | 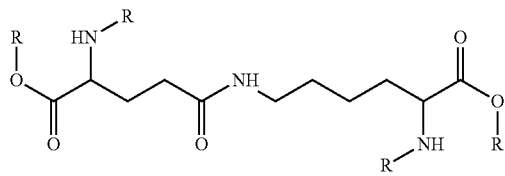 |
| BSA GGEL coupled with glutaraldehyde (GGEL-BSA) | 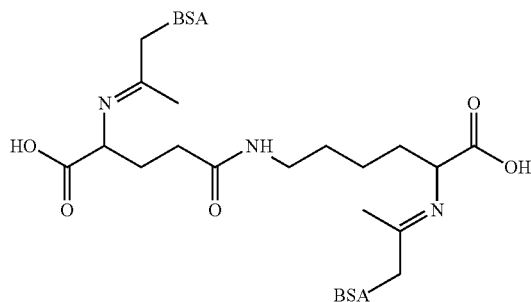 |
| GGEL formed by coupling Cbz-Lys-Ome to BSA (ZLysOme-BSA) | 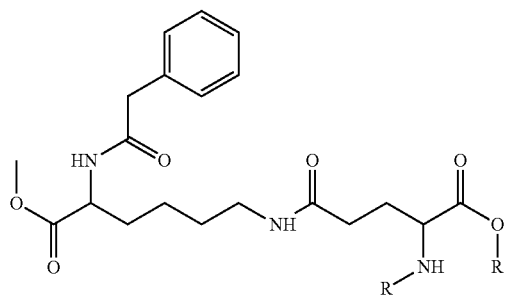 |
| GGEL formed by coupling Cbz-Glu-Oter to BSA (ZGluOter-BSA) | 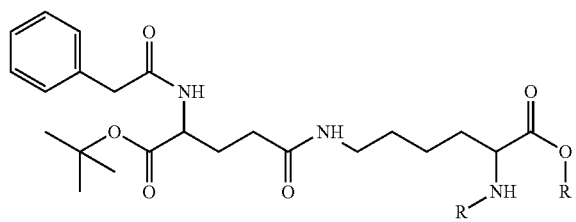 |

TABLE 3

Antigenic proteins used for specificity determination as negative control.

| | |
|---|---|
| Spd coupled to polyGlutamic acid bis-(poly(glutamic acid))-spermidine mimic polyamine crosslink bis-Glu-Spd | 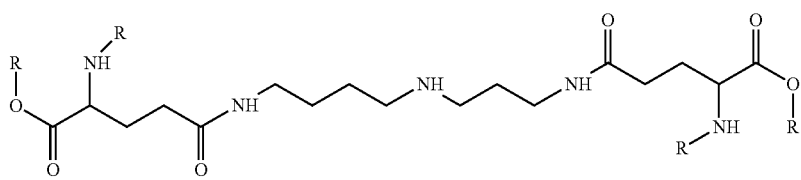 |
| Boc-Glycine coupled to BSA (Boc-Gly-BSA) mimic Ubiquitinylation/Sumolytation crosslink | 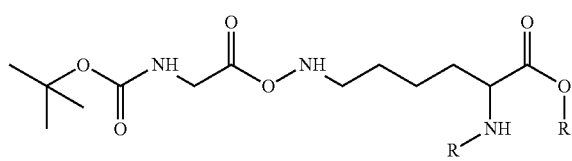 |

TABLE 3-continued

Antigenic proteins used for specificity determination as negative control.

Acetylated BSA (BSA-Ac) mimic acetylation of lysine

Antibody Specificity Determination. Competition ELISA.

Selected clones were tested using a competitive ELISA test in order to determine the specificity of the clones. Therefore BSA-GGEL was adsorbed on microtiter plate at a concentration of 10 µg/mL in a bicarbonate buffer pH 9.50. A concentration of purified antibody (1G1h1 at 2 µg/mL or AB424 at 0.5 µg/mL) was incubated with each competitor antigenic protein of Tables 2 and 3, diluted in cascade two by two with a starting concentration of 5 µg/mL. After 1 hour of incubation at 37° C., the microtiter plate was washed and a goat anti-mouse (H+L) peroxidase conjugate was added for 30 minutes at 37° C. Revelations were performed using TMB for 5 minutes and reaction were stopped using $H_2SO_4$, 2N. Absorbance values were determined at 450 nm with Spectramax i3® automated microplate reader (Molecular Devices, Sunnydale, USA). Wells were given four rinses with PBST between each incubation. Working volumes were 100 µL per well, and control wells were incubated with culture medium. The comparison of each antigenic protein were performed by calculated the inhibitory concentration of 50% of the initial signal (without any competitor).

Results

A so-called 1G1h1 anti-GGEL monoclonal antibody comprising a variable domain of heavy chain of sequence (SEQ ID NO: 1)
QVQLQQPGTELVKPGASVKLSCKASGYTFTSYWMHWVKQRPGQGLEWIGN

INPSNGGTNYNEKFKSKATLTVDKSSSTAYMQLSSLTSEDSAVYYCARSG

LLLWSPWFAYWGQGTLVTVS, and a variable domain of light chain of sequence (SEQ ID NO: 2)
DIQMTQSPASLSASVGETVTITCRASENIYSYLAWYQQKQGKSPQLLVY

NAKTLAEGVPSRFSGSGSGTQFSLKINSLQPEDFGSYYCQHHYGTPFT

FGSGTKLEIKR was isolated. CDRs, as identified according to the IMGT definition, are represented in bold and underlined characters.

Specificity of the isolated 1G1h1 antibody was determined and compared to the previously characterized commercial AB424 antibody (Thomas et al. 2004, J. Immunol. Methods 292, 83-95).

It was determined that both 1G1h1 and AB424 antibodies detect D-dimer, with a non-significant difference in their titers (2.5 µg/mL for 1 G1 h1 and 0.6 µg/mL for AB424).

Specificity of 1G1h1 and AB424 antibodies was further determined using antigenic proteins described in Tables 2 and 3 in a competitive ELISA against GGEL. The results are shown in Table 4.

An $IC_{50}$ is considered as significantly different from another $IC_{50}$ when one log of difference is observed between the two $IC_{50}$.

TABLE 4

Specificity of anti-GGEL antibodies 1G1h1 and AB424

| | $IC_{50}$ in nM | | | | | |
|---|---|---|---|---|---|---|
| | GGEL like proteins | | | Negative controls | | |
| mAb | GGEL-BSA | ZGluOter-BSA | ZLysOme-BSA | Spd-pGlu | BSA-Ac | Boc-Gly-BSA |
| 1G1h1 | 1.09 | 3.89 | 3.47 | >25000 | >45.3 | >45.3 |
| AB424 | 8.68 | >400 | 4.89 | 2700 | >45.3 | >45.3 |

$IC_{50}$ of each antigenic protein was evaluated, and for 1G1h1 one log of decrease was observed between GGEL-like proteins (Table 2) and negative control proteins (Table 3).

It was concluded that the 1G1h1 antibody is specific for GGEL-BSA, ZGluOter-BSA and ZLysOme-BSA antigenic proteins, therefore that the antibody is specific for the GGEL isopeptide versus other crosslinked or modified lysines.

Conversely, the AB424 antibody cross-reacts with the isopeptide $N^1,N^8$bis(gamma-glutamyl) spermidine but does not bind the GGEL competitor antigen ZGluOter-BSA.

Accordingly, that 1G1h1 antibody has enhanced specificity for GGEL compared to the commercial AB424 antibody.

Example 2: Quantification of Gamma-Glutamyl-L-Epsilon-Lysine (GGEL) with the 1G1h1 Monoclonal Antibody Materials & Methods GGEL Quantification by Competitive ELISA. Competitive ELISA.

BSA-GGEL was adsorbed on microtiter plate at a concentration of 10 µg/mL in a 50 mM bicarbonate solution pH 9.50. Plates were incubated overnight at laboratory temperature. Saturation was performed with a phosphate buffer 0.1 M supplemented of BSA 0.5% and sucrose 5% (FIG. 3, step 1). Samples diluted were added in presence of antibody solution for 1 hour at 37° C., BZGO with a precise number of GGEL "coated" on were diluted two by two and used as standard (FIG. 3, step 2 and 3). After three washes with PBST, secondary antibody diluted 1 in 2000 PBST was incubated 30 minutes at 37° C. Revelation were performed using TMB for 5 minutes and reaction were stopped using $H_2SO_4$, 2N (FIG. 3, step 4). Absorbance values were determined at 450 nm with Spectramax i3® automated microplate reader (Molecular Devices, Sunnydale, USA). GGEL quantification was performed using standard plotted on a 4 parameters line using GrapPad Prism version 5.0 (GraphPad software, San Diego, USA). The threshold for positivity of results was determined considering the mean of the blank added to 3.33 standard deviation.

Results

The 1G1h1 antibody was used for GGEL quantification by a competitive ELISA Standardized N-alpha-Cbz-Glutamic acid Methyl Ester (Z-GluOme) coupled to BSA (BZGO) with known amounts of GGEL were used as standard for the quantification of GGEL. FIG. 2 displays the standard curve for quantification of GGEL concentration, which was calculated using 4-Parameter line using SoftMax Pro 6.5.

Curve fit using 4-Parameter line was as follows:

$$y = D + \frac{A - D}{1 + \left(\frac{X}{C}\right)^B}$$

TABLE 5

GGEL standard curve parameters

| | Parameter | Estimated value | Std. error | Confidence interval |
|---|---|---|---|---|
| Standard curve | A | 0.840 | 0.047 | [0.691; 0.989] |
| $R^2 = 0.998$ | B | 1.193 | 0.180 | [0.621; 1.766] |
| $EC_{50} = 3.274$ | C | 3.274 | 0.356 | [2.142; 4.406] |
| | D | 0.079 | 0.028 | [−0.011; 0.170] |

This anti-GGEL 1G1h1 monoclonal antibody was further used in the following experiments.

Example 3: In Vitro Detection of Free GGEL Released by Apoptotic Cells

Materials & Methods
Cell Lines.

Cell line used for apoptosis induction was Human promyelocytic leukemia cells, HL-60. HL-60 were cultured in RPMI media supplemented with 10% Fetal Calf Serum (FCS), 1% Streptomycin/Penicillin and 200 mM L-Glutamine.

Induction of apoptosis.

Cells were plated at 1×10E6 cells/mL in cell culture medium described before. Induction of apoptosis were done using staurosporine at a concentration of 1 µmol/L during 8 hours. Staurosporine is an alkaloid isolated from the culture broth of *Streptomyces staurosporesa*. It is a potent, cell permeable protein kinase C inhibitor and other kinases such as PKA, PKG, CAMKII and Myosin light chain kinase (MLCK). At 0.2-1 µM, staurosporine induces cell apoptosis. After treatment, cells were then centrifuged at 800 g, 10 min and supernatant were used for GGEL quantification.

GGEL Quantification

GGEL quantification by competitive ELISA. Competitive ELISA. BSA-GGEL were adsorbed on microtiter plate at a concentration of 10 µg/mL in a 50 mM bicarbonate solution pH9.50. Plates were incubated overnight at laboratory temperature. Saturation was perform with a phosphate buffer 0.1 M supplemented of BSA 0.5% and sucrose 5% (FIG. 3, step 1). Cells supernatant were added in presence of antibody solution for 1 hour at 37° C., BZGO with a precise number of GGEL "coated" on were diluted two by two and used as standard (FIG. 3, step 2 and 3). After three washes with PBST, secondary antibody diluted 1 in 2000 PBST was incubated 30 minutes at 37° C. Revelation were performed using TMB for 5 minutes and reaction were stopped using H2SO4, 2N (FIG. 3, step 4). Absorbance values were determined at 450 nm with Spectramax i3® automated microplate reader (Molecular Devices, Sunnydale, USA). GGEL quantification was performed using standard plotted on a 4 parameters line using GrapPad Prism version 5.0 (GraphPad software, San Diego, USA).

Statistical Analysis.

Values are expressed as mean±SD or frequencies and proportions. Differences between groups were determined by unpaired t test, Chi-square, Fisher's exact test or ANOVA, where appropriate. P<0.05 was considered statistically significant. Analysis was performed using GraphPad prism version 5.0 (GraphPad software, San Diego Calif. USA).

Results

FIG. 3 shows the results of GGEL quantification with the 1G1h1 antibody in HL-60 cells after induction of apoptosis by staurosporin, or without staurosporin treatment. GGEL concentration in HL-60 cells induced into apoptosis was significantly different from HL-60 cells non-induced into apoptosis.

Example 4: Identification of Gamma-Glutamyl-L-Epsilon-Lysine (GGEL) as a Biomarker of Early Sepsis Materials & Methods The inventors have sought to determine whether GGEL in plasma can be measured in an Enzyme Immuno Assay (EIA). The protocol was based on a GGEL quantification competitive EIA (see example 2 & 3) with plasma samples diluted at 1/20. Control plasma samples from 10 healthy individuals were used to determine the background level of GGEL in normal plasma. The tests were performed on 22 sepsis samples, obtained at day 1 and day 3 from 11 patients. Day 1 is the day on which the patient was hospitalized and was detected with fever and a symptomatic feature of SIRS (see table 1). In order to distinguish positive from negative tests, a cut-off value was calculated from the 10 control plasma samples.

Comparison of each group was evaluated using ANOVA 1-way.

ROC curve Analysis was performed using GraphPad prism version 5.0 (GraphPad software, San Diego Calif. USA). Blank plasma was designated as controls and sepsis plasmas as patients.

Results

Using this test, it was demonstrated that sepsis plasma can be discriminated from blank plasma as a significant enhancement of GGEL concentration was observed for group D+1 and D+3 in comparison to blank samples (FIG. 4). Accordingly, GGEL presence is an effective biomarker of early sepsis.

However, day 1 plasma may not be discriminated from day 3 samples. Yet by analyzing the results for each patient, an increase of GGEL biomarker from day 1 to day 3 has been detected and observed for 8 patients out of 11.

The marker diagnostic performance could be characterised by sensitivity, which represents its ability to detect the sepsis population, and specificity, which represents its ability to detect the control population.

Blank plasma were used in order to determinate the threshold of the test (V=µ×3 SD). Specificity and sensitivity were obtained resulting in a specificity of 91% for D+1 group, 100% for D+3 group and 95.45% for the merged group (D+1+D+3) (Table 6). A ROC curve of the test was further obtained (FIG. 5 and Table 7).

TABLE 6

Specificity of GGEL quantitation for sepsis diagnosis

| Group | True positive (TP) | False positive (FP) | True negative (TN) | False negative (FN) | specificity |
|---|---|---|---|---|---|
| D1 | 10 | 0 | 0 | 1 | 91% |
| D3 | 11 | 0 | 0 | 0 | 100% |
| D1 + D3 | 21 | 0 | 0 | 1 | 95.45% |

TABLE 7

Diagnosis potential (mROC approach) of GGEL for sepsis diagnosis

| | |
|---|---|
| Area under the ROC curve | 0.9773 |
| Std. Error | 0.02730 |
| 99% confidence interval | 0.9069 to 1.048 |
| P value | 0.002851 |

Example 5: Dosage of Gamma-Glutamyl-L-Epsilon-Lysine (GGEL) in Different Pathologies Materials and Methods Samples Plasma were obtained from the Centre de Ressources Biologiques from Hôpital Lariboisière, Paris, France. 364 plasmas sample were obtained representing 4 different clinical pathology: heart/respiratory failure (HRF) (n=106), Trauma (n=90), Septic shock (n=130) or Severe Sepsis (n=38), at two different time points, T1 which were collected at the entry in hospital, and T2 for the coming out of the hospital.

GGEL Quantification by Competitive ELISA. Competitive ELISA

Antigen BSA-GGEL was adsorbed on a microtiter plate with a 50 mM bicarbonate solution pH 9.50. Plates were incubated overnight at room temperature. Saturation was performed with a phosphate buffer 0.1M supplemented with BSA 0.5% and sucrose 5%. Diluted samples were added in presence of the anti-GGEL antibody solution for 1 hour at 37° C., BZGO with a precise number of GGEL "coated" on were diluted two by two and used as standard. After three washes with PBST, revelation was performed using TMB for 10 minutes and reaction was stopped using $H_2SO_4$, 2N. Absorbance values were determined at 450 nm with Spectramax i3® automated microplate reader (Molecular Devices, Sunnydale, Calif., USA). GGEL quantification was performed using standard plotted on a semi-log line using SoftMaxPro 6.5.1 (Molecular Devices, Sunnydale, USA).

Statistical Analysis

Variables were analyzed by descriptive statistics to evaluate the clinical characteristics of the cases. All are reported as mean±S.D, and were analyzed using one-way analysis of variance to estimate the presence of any statistical difference between the studied samples. Two-tailed probability values are listed in the table and the level of statistical significance was set up at p<0.05. All statistical analyses were performed with GraphPad Prism version 5.0 (GraphPad software, San Diego, Calif., USA) or JMP software version 12 (SAS Institute Inc. Cary, N.C., USA).

Results

Comparison of GGEL Concentration Between Different Pathologies

The level of GGEL concentration in plasma was significantly higher in Trauma group than in the others (p<0.01). A higher level of GGEL concentration than in Normal samples (22 $\mu mol \cdot L^{-1}$) was observed in Septic Shock (39.29 $\mu mol \cdot L^{-1}$) and Severe Sepsis samples (28.47 $\mu mol \cdot L^{-1}$) but results were not significant (FIG. 7).

Comparison of GGEL Concentration Between the Different Time Point by Pathologies The level of GGEL significantly increase from T1 to T2 in Trauma from a T1-mean of 45.61±19.72 to 111.14±24 $\mu mol \cdot L^{-1}$ (FIG. 8). For the other pathologies, a non-significant increase of GGEL concentration in plasma was observed.

Comparison a GGEL Concentration Per Patient by Pathologies

For each patient plasma, the modification of GGEL concentration was calculated as follow $\Delta GGEL=[GGEL]_{T2}-[GGEL]_{T1}$. The mean of $\Delta GGEL$ per pathologies were analyzed with result for Trauma and Septic shock respectively 38.75±22.78 and 21.58±10.2 $\mu mol \cdot L^{-1}$, higher than HRF and Severe sepsis (Table 8). However non-significant results were noticed between the different pathologies.

TABLE 8

ΔGGEL concentration per patient by pathologies

| Pathologies | Mean ($\mu mol \cdot L^{-1}$) | Standard Deviation ($\mu mol \cdot L^{-1}$) |
|---|---|---|
| HRF | 3.5325 | 6.451 |
| Septic Shock | 21.5827 | 10.021 |
| Severe Sepsis | 9.7431 | 7.899 |
| Trauma | 38.7504 | 22.782 |

The invention claimed is:

1. An isolated monoclonal antibody specific for gamma-glutamyl-L-epsilon-Lysine (GGEL) which comprises CDR-H1 of sequence SEQ ID NO:3, CDR-H2 of sequence SEQ ID NO:4, CDR-H3 of sequence SEQ ID NO:5, CDR-L1 of sequence SEQ ID NO:6, CDR-L2 of sequence SEQ ID NO:7, and CDR-L3 of sequence SEQ ID NO:8.

2. The isolated monoclonal antibody according to claim 1 which comprises a variable domain of heavy chain of sequence SEQ ID NO:1, or a sequence at least 85% identical to SEQ ID NO: 1.

3. The isolated monoclonal antibody according to claim 1 which comprises a variable domain of light chain of sequence SEQ ID NO:2, or a sequence at least 85% identical to SEQ ID NO:2.

4. A method for measuring the level of gamma-glutamyl-L-epsilon-Lysine (GGEL) in a sample, which comprises:
   a) contacting a sample with the monoclonal antibody specific for GGEL according to claim 1; and
   b) measuring the level of complexes formed with the monoclonal antibody specific for GGEL;
   wherein the level of GGEL in the sample is deduced from the level of complexes formed with the monoclonal antibody specific for GGEL.

5. An ex vivo method for the monitoring of apoptosis in a subject, which comprises:

a) measuring the level of free gamma-glutamyl-L-epsilon-Lysine (GGEL) isopeptide in a plasma sample of the subject with an immunoassay using the monoclonal antibody according to claim 1;
   b) comparing said measured level of free GGEL with a control; and
   c) monitoring apoptosis in said subject based on the comparison with the control.

6. The method according to claim 5, wherein monitoring apoptosis in said patient based on the comparison with the control is performed by:
   (i) if the control is derived from a healthy subject or population of healthy subjects, determining that apoptosis is upregulated in the subject if the level of free GGEL in the plasma sample of the subject is greater than the level of free GGEL in the control, or determining that apoptosis is downregulated in the subject if the level of free GGEL in the plasma sample of the subject is lower than the level of free GGEL in the control; or
   (ii) if the control is derived from a subject or population of subjects suffering from disease associated with upregulated apoptosis, determining that apoptosis is upregulated in the subject if the level of free GGEL in the plasma sample of the subject is equal or greater than the level of free GGEL in the control; or (iii) if the control is derived from a subject or population of subjects suffering from disease associated with downregulated apoptosis, determining that apoptosis is downregulated in the subject if the level of free GGEL in the plasma sample of the subject is equal or lower than the level of free GGEL in the control.

7. The method according to claim 5, wherein monitoring of apoptosis enables for diagnosing a disease associated with dysregulated apoptosis, upregulated or downregulated apoptosis.

8. The method according to claim 7, wherein monitoring of apoptosis enables for diagnosing sepsis.

9. The method according to claim 4, wherein the level of free GGEL is measured by an ELISA, indirect, competitive or sandwich.

10. A method for monitoring effectiveness of an apoptosis inducing treatment in a subject, which comprises:
   a) measuring the level of free gamma-glutamyl-L-epsilon-Lysine (GGEL) isopeptide in a plasma sample of a subject undergoing an apoptosis inducing treatment, with a method according to claim 4;
   b) repeating the measurement of step a) in time; and
   c) deducing that the apoptosis inducing treatment is effective if the level of free GGEL increases over time, or that the apoptosis inducing treatment is ineffective if the level of free GGEL is unchanged or decreases over time.

11. A method for monitoring effectiveness of an apoptosis inhibiting treatment in a subject is provided, which comprises:
   a) measuring the level of free gamma-glutamyl-L-epsilon-Lysine (GGEL) isopeptide in a plasma sample of a subject undergoing an apoptosis inhibiting treatment, with a method according to claim 4;
   b) repeating the measurement of step a) in time; and
   c) deducing that the apoptosis inhibiting treatment is effective if the level of free GGEL decreases over time, or that the apoptosis inhibiting treatment is ineffective if the level of free GGEL is unchanged or increases over time.

12. A method of treating a disease associated with dysregulated apoptosis in a subject in need thereof, which comprises:
   a) administering an apoptosis modulating treatment to a subject treating suffering from a disease associated with dysregulated apoptosis
   b) monitoring if said treatment modulates apoptosis in the subject by implementing the method of monitoring of apoptosis according to claim 5; and
   c) continuing or modifying the apoptosis modulating treatment based on the result of monitoring of step b).

13. A kit for the monitoring of apoptosis which comprises:
   a) a monoclonal antibody specific for gamma-glutamyl-L-epsilon-Lysine (GGEL) as defined in claim 1; and
   b) a control.

14. A method of treating sepsis in a subject in need thereof, which comprises:
   a) diagnosing sepsis in a subject by an ex vivo method of diagnostic of sepsis according to claim 8; and
   b) administering a therapeutic treatment against sepsis to the subject diagnosed as suffering from sepsis.

15. A lateral flow immunoassay device which comprises a monoclonal antibody specific for gamma-glutamyl-L-epsilon-Lysine (GGEL) as defined in claim 1.

* * * * *

SEQUENCE LISTING

<160> NUMBER OF SEQ ID NOS: 8

<210> SEQ ID NO 1
<211> LENGTH: 120
<212> TYPE: PRT
<213> ORGANISM: Mus musculus

<400> SEQUENCE: 1

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

```
Trp Met His Trp Val Lys Gln Arg Pro Gly Gln Gly Leu Glu Trp Ile
            35                  40                  45

Gly Asn Ile Asn Pro Ser Asn Gly Gly Thr Asn Tyr Asn Glu Lys Phe
 50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Gly Leu Leu Leu Trp Ser Pro Trp Phe Ala Tyr Trp Gly
            100                 105                 110

Gln Gly Thr Leu Val Thr Val Ser
        115                 120

<210> SEQ ID NO 2
<211> LENGTH: 108
<212> TYPE: PRT
<213> ORGANISM: Mus musculus

<400> SEQUENCE: 2

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
 50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Phe
                85                  90                  95

Thr Phe Gly Ser Gly Thr Lys Leu Glu Ile Lys Arg
            100                 105

<210> SEQ ID NO 3
<211> LENGTH: 7
<212> TYPE: PRT
<213> ORGANISM: Artificial Sequence
<220> FEATURE:
<223> OTHER INFORMATION: CDR-H1

<400> SEQUENCE: 3

Gly Tyr Thr Phe Thr Ser Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: CDR-H2

<400> SEQUENCE: 4

Asn Pro Ser Asn Gly Gly
1               5

<210> SEQ ID NO 5
<211> LENGTH: 12
<212> TYPE: PRT
<213> ORGANISM: Artificial Sequence
<220> FEATURE:
```

```
<223> OTHER INFORMATION: CDR-H3

<400> SEQUENCE: 5

Ser Gly Leu Leu Leu Trp Ser Pro Trp Phe Ala Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: CDR-L1

<400> SEQUENCE: 6

Arg Ala Ser Glu Asn Ile Tyr Ser Tyr Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: CDR-L2

<400> SEQUENCE: 7

Asn Ala Lys Thr Leu Ala Glu
1               5

<210> SEQ ID NO 8
<211> LENGTH: 9
<212> TYPE: PRT
<213> ORGANISM: Artificial Sequence
<220> FEATURE:
<223> OTHER INFORMATION: CDR-L3

<400> SEQUENCE: 8

Gln His His Tyr Gly Thr Pro Phe Thr
1               5
```